US008613934B2

(12) United States Patent
Raviv et al.

(10) Patent No.: US 8,613,934 B2
(45) Date of Patent: *Dec. 24, 2013

(54) CELLULAR AND VIRAL INACTIVATION

(75) Inventors: Yossef Raviv, Rockville, MD (US); Julie M. Belanger, Frederick, MD (US); Mathias Viard, Frederick, MD (US); Robert Blumenthal, Bethesda, MD (US); Julian W. Bess, Jr., Frederick, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 523 days.

This patent is subject to a terminal disclaimer.

(21) Appl. No.: 12/847,231

(22) Filed: Jul. 30, 2010

(65) Prior Publication Data

US 2011/0038890 A1 Feb. 17, 2011

Related U.S. Application Data

(63) Continuation-in-part of application No. PCT/US2009/000623, filed on Jan. 30, 2009, and a continuation-in-part of application No. 11/525,250, filed on Sep. 21, 2006, now Pat. No. 8,268,602, which is a continuation of application No. PCT/US2005/009559, filed on Mar. 22, 2005.

(60) Provisional application No. 61/025,424, filed on Feb. 1, 2008, provisional application No. 61/088,294, filed on Aug. 12, 2008, provisional application No. 60/555,268, filed on Mar. 22, 2004.

(51) Int. Cl.
*A61K 39/12* (2006.01)
*C12N 7/06* (2006.01)
*C12N 13/00* (2006.01)
*A61P 31/12* (2006.01)
*A61P 37/04* (2006.01)

(52) U.S. Cl.
USPC ............... 424/204.1; 435/238; 435/173.3

(58) Field of Classification Search
None
See application file for complete search history.

(56) References Cited

U.S. PATENT DOCUMENTS

| 4,962,091 | A | 10/1990 | Eppstein et al. |
| 5,232,844 | A | 8/1993 | Horowitz et al. |
| 5,780,287 | A | 7/1998 | Kraus et al. |
| 6,776,824 | B2 | 8/2004 | Wen |
| 8,268,602 | B2 * | 9/2012 | Raviv et al. ............. 435/173.3 |
| 8,278,083 | B2 * | 10/2012 | Raviv et al. ............. 435/173.3 |
| 2009/0297558 | A1 | 12/2009 | Raviv et al. |

FOREIGN PATENT DOCUMENTS

| WO | WO 94/07529 A1 | 4/1994 |
| WO | WO 94/28120 A1 | 12/1994 |
| WO | WO 99/41360 A1 | 8/1999 |
| WO | WO 2005/093049 A1 | 10/2005 |
| WO | WO 2008/054481 A2 | 5/2008 |
| WO | WO 2009/131606 A2 | 10/2009 |

OTHER PUBLICATIONS

Zakowski et al. (Journal of Virology. 1980; 36 (1): 93-102).*
Salk et al. (Journal of Experimental Medicine. 1940; 30: 729-745).*
Belanger et al. (Photochemistry and Photobiology. 2010; 86: 1099-1108).*
Database Biosis [Online] Biosciences Information Service, Philadelphia, PA, US; 1979, Heinz F X et al., "Protease Treatment and Chemical Cross Linking of a Flavivirus Tick-Borne Encephalitis Virus" XP002553758 Database accession No. PREV198069006818 & Archives of Virology, vol. 60, No. 3-4, 1979, pp. 207-216.
Anonymous: "NCI-CCR Initiatives. Nanotechnology" Selective Inactivation of Pathogenic Organisms, Viruses, and Tumor Cells for Vaccine Development by 5-Iodonaphthyl-1-azide (INA) or Other Hydrophobic Reactive Probes, Apr. 24, 2006, XP00253757, Retrieved from the Internet: URL:http://web.archive.org/web/20060426015039/http://ccr.cancer.gov/initiatives/nanotechnology.asp> [retrieved on Oct. 29, 2009].
Abels et al., "In vivo kinetics and spectra of 5-aminolaevulinic acid-induced fluorescence in an amelanotic melanoma of the hamster," Br J Cancer, 1994, 70, 826-833.
Arthur LO, et al., Cellular proteins bound to immunodeficiency viruses: implications for pathogenesis and vaccines. Science. Dec. 18, 1992;258(5090):1935-8.
Arthur LO, et al., Chemical inactivation of retroviral infectivity by targeting nucleocapsid protein zinc fingers: a candidate SIV vaccine. AIDS Res Hum Retroviruses. Oct. 1998;14 Suppl 3:S311-9.
Australian Application Serial No. 2005227320, Office Action mailed Jul. 1, 2009, 2 pages.
Benveniste et al., Characterization of clones of HIV-1 infected HuT 78 cells defective in gag gene processing and of SIV clones producing large amounts of envelope glycoprotein. J Med Primatol. 1990;19(3-4):351-66.
Bercovici, T., "5-[125I]Iodonaphthyl Azide, a Reagent to Determine the Penetration of Proteins into the Lipid Bilayer of Biological Membranes," Biochemistry, Apr. 18, 17(8), 1978, 1484-1489.
Berger EA et al., Chemokine receptors as HIV-1 coreceptors: roles in viral entry, tropism, and disease. Annu Rev Immunol. 1999;17:657-700.
Bess JW Jr, et al., Microvesicles are a source of contaminating cellular proteins found in purified HIV-1 preparations. Virology. Mar. 31, 1997;230(1):134-44.
Chan DC, et al., Core structure of gp41 from the HIV envelope glycoprotein. Cell. Apr. 18, 1997;89(2):263-73.

(Continued)

*Primary Examiner* — Shanon A Foley
(74) *Attorney, Agent, or Firm* — Woodcock Washburn LLP

(57) ABSTRACT

The invention involves inactivation of viral populations by treating the viral populations with a compound to crosslink proteins in the viral membrane, UV irradiation and further inactivation of the viruses using detergent(s). According to the invention, this method preserves the native structure of viral epitopes so that the inactivated viral preparations can be used in immunological compositions that will inhibit and/or prevent viral infection when administered to an animal.

17 Claims, 17 Drawing Sheets

(56) References Cited

OTHER PUBLICATIONS

Chan DC, et al., Evidence that a prominent cavity in the coiled coil of HIV type 1 gp41 is an attractive drug target. Proc Natl Acad Sci U S A. Dec. 22, 1998;95(26):15613-7.
Chan DC, et al., HIV entry and its inhibition. Cell. May 29, 1998;93(5):681-4.
Chanh et al., "Neutralization of HIV-1 and inhibition of HIV-1-induced syncytia by 1,8-naphthalimide photoactive compound," AIDS Res Hum Retroviruses, Sep. 1993, 9(9), 891-896.
Chanh, T.C. et al., "Photodynamic inactivation of simian immundodeficiency virus," Journal of Virological Methods, 1989, 26(1), 125-131.
Chen CH, et al., A molecular clasp in the human immunodeficiency virus (HIV) type 1 TM protein determines the anti-HIV activity of gp41 derivatives: implication for viral fusion. J Virol. Jun. 1995;69(6):3771-7.
Chen Z, et al., Primary SIVsm isolates use the CCR5 coreceptor from sooty mangabeys naturally infected in west Africa: a comparison of coreceptor usage of primary SIVsm, HIV-2, and SIVmac. Virology. Jun. 20, 1998;246(1):113-24.
Chinese Application Serial No. 200580009241.1, Office Action mailed Jul. 28, 2008, 6 pages.
Dimitrov DS, Cell biology of virus entry. Cell. Jun. 23, 2000;101(7):697-702.
Dimitrov DS, et al., Kinetics of HIV-1 interactions with sCD4 and CD4+ cells: implications for inhibition of virus infection and initial steps of virus entry into cells. Virology. Apr. 1992;187(2):398-406.
Doms RW, Beyond receptor expression: the influence of receptor conformation, density, and affinity in HIV-1 infection. Virology. Oct. 25, 2000;276(2):229-37.
Düzgünes N, et al., Fusion of HIV-1 and SIVmac with liposomes and modulation of HIV-1 infectivity. Adv Exp Med Biol. 1991;300:167-89.
European Application Serial No. 05760441.5, Office Action mailed Jul. 8, 2008, 5 pages.
Frey S, et al., Temperature dependence of cell-cell fusion induced by the envelope glycoprotein of human immunodeficiency virus type 1. J Virol. Mar. 1995;69(3):1462-72.
Furuta RA, et al., Capture of an early fusion-active conformation of HIV-1 gp41. Nat Struct Biol. Apr. 1998;5(4):276-9. Erratum in: Nat Struct Biol Jul. 1998;5(7):612.
Gallo SA, et al., HIV-1 gp41 six-helix bundle formation occurs rapidly after the engagement of gp120 by CXCR4 in the HIV-1 Env-mediated fusion process. Biochemistry. Oct. 16, 2001;40(41):12231-6.
Gruenert, D.C. et al. "Repair of ultraviolet damage in human cells also exposed to agents that cause strand breaks, crosslinks, monoadducts and alkylations," Chem Biol Interact, Jan. 1981, 33(2-3), 163-77.
Hanson, C.V., "Rapid Photochemical Inactivation of Human Immunodeficiency Virus HIV," Journal of Cellular Biochemistry, Suppl. 11, Pt D, Symposium on Human retroviruses, Cancer and Aids: Approaches to Prevention and Therapy, 1987, 65.
Hoekstra D, et al., Fluorescence method for measuring the kinetics of fusion between biological membranes. Biochemistry. Nov. 20, 1984;23(24):5675-81.
Hug P, et al., Glycosphingolipids promote entry of a broad range of human immunodeficiency virus type 1 isolates into cell lines expressing CD4, CXCR4, and/or CCR5. J Virol. Jul. 2000; 74(14):6377-85.
International Application Serial No. PCT/US2005/009559, International Search Report mailed Sep. 12, 2005, 9 pages.
International Application Serial No. PCT/US2005/009559, Written Opinion mailed Sep. 12, 2005, 6 pages.
International Application Serial No. PCT/US2007/007338, Search Report mailed Aug. 5, 2008, 8 pages.
International Application Serial No. PCT/US2007/007338, Written Opinion mailed Aug. 5, 2008, 7 pages.
Jernigan KM et al., Varying effects of temperature, Ca(2+) and cytochalasin on fusion activity mediated by human immunodeficiency virus type 1 and type 2 glycoproteins. FEBS Lett. Jun. 2, 2000;474(2-3):246-51.
Jiang S, et al., Inhibition of HIV-1 infection by a fusion domain binding peptide from the HIV-1 envelope glycoprotein GP41. Biochem Biophys Res Commun. Sep. 15, 1993;195(2):533-8.
Johnson, J.I. et al., "Relationships between drug activity in NCI preclinical in vitro and in vivo models and early clinical trials," British J of Cancer, 2001, 84(10), 1424-1431.
Jonak ZL, et al., A human lymphoid recombinant cell line with functional human immunodeficiency virus type 1 envelope. AIDS Res Hum Retroviruses. Jan. 1993;9(1):23-32.
Kowalski M, et al., Functional regions of the envelope glycoprotein of human immunodeficiency virus type 1. Science. Sep. 11, 1987;237(4820):1351-5.
Krumbiegel M, et al., Kinetics of the low pH-induced conformational changes and fusogenic activity of influenza hemagglutinin. Biophys J. Dec. 1994;67(6):2355-60.
LaCasse RA, et al.,Fusion-competent vaccines: broad neutralization of primary isolates of HIV. Science. Jan. 15, 1999;283(5400):357-62.
Liao Z, et al., Increased infectivity of HIV type 1 particles bound to cell surface and solid-phase ICAM-1 and VCAM-1 through acquired adhesion molecules LFA-1 and VLA-4. AIDS Res Hum Retroviruses. Mar. 1, 2000;16(4):355-66.
Melikyan GB, et al., Evidence that the transition of HIV-1 gp41 into a six-helix bundle, not the bundle configuration, induces membrane fusion. J Cell Biol. Oct. 16, 2000;151(2):413-23.
Merezhinskaya N, et al., Reversible penetration of alpha-glutathione S-transferase into biological membranes revealed by photosensitized labelling in situ. Biochem J. Nov. 1, 1998;335 ( Pt 3):597-604.
Moreno, G. et al., "Photosensitization of mammalian cells by psoralens and porphyrins," Biochimie, Jun. 1986, 68(6), 869-73.
Muñoz-Barroso I, et al., Dilation of the human immunodeficiency virus-1 envelope glycoprotein fusion pore revealed by the inhibitory action of a synthetic peptide from gp41. J Cell Biol. Jan. 26, 1998;140(2):315-23.
Nitzan et al., "Effect of Photoactivated Hematoporphyrin Dertivative on the Viability of *Staphylococcus aureus*," Current Microbiology, 1983, 8, 279-284.
Ott DE, et al., The majority of cells are superinfected in a cloned cell line that produces high levels of human immunodeficiency virus type 1 strain MN. J Virol. Apr. 1995;69(4):2443-50.
Pak, C.C. et al., "Conformational Changes and Fusion Activity of Vesicular Stomatitus Virus Glycoprotein: [125I]Iodonaphthyl Azide Photolabeling Studies in Biological Membranes," Biochemistry, Jul. 22, 1997, 36(29), 8890-8896.
Pak, C.C., "Detection of Influenza Hemagglutinin Interaction with Biological Membranes by Photosensitized Activation of [125I]Iodonaphthylazide," Journal of Biological Chemistry, May 20, 1994, 269(20), 14614-14619.
Perlin, M. et al., "Photodymic Inactivation of Influenza and Herpesviruses by Hematoporphyrin," Antiviral Research, 1987, 7(1), 43-52.
Rai, S. et al., "Dramatic improvements in viral inactivation with brominated psoralens, naphthalenes and anthracenes," Photochem Photobiol, Jul. 1993, 58(1), 59-65.
Raviv Y, et al., P-glycoprotein-overexpressing multidrug-resistant cells are resistant to infection by enveloped viruses that enter via the plasma membrane. FASEB J. Mar. 2000;14(3):511-5.
Raviv Y, et al., Photosensitized labeling of a functional multidrug transporter in living drug-resistant tumor cells. J Biol Chem. Mar. 5, 1990;265(7):3975-80.
Raviv Y, et al., Selective labeling of proteins in biological systems by photosensitization of 5-iodonaphthalene-1-azide. Proc Natl Aced Sci U S A. Sep. 1987;84(17):6103-7.
Raviv, Y. et al., "Detection of nearest neighbors to specific fluorescently tagged ligands in rod outer segment and lymphocyte plasma membranes by photosensitization of 5-iodonaphthyl 1-azide," Biochemistry, Feb. 7, 1989, 28(3), 1313-1319.
Raviv, Y. et al., "Quantitative Measurement of Fusion of HIV-1 and SIV with Cultured Cells Using Photosensitized Labeling," Virology, Feb. 15, 2002, 293(2), 243-251, http://www.idealibrary.com.
Raviv, Y. et al., "Selective photoinduced uncoupling of the response of adenylate cyclase to gonadotropins by 5-iodonaphthyl 1-azide," Biochemistry, 1984, 1984, 23(3), 503-508.

(56) References Cited

OTHER PUBLICATIONS

Rossio, J.L. et al., "Inactivation of human immunodeficiency virus type 1 infectivity with preservation of conformational and functional integrity of virion surface proteins," J Virol, Oct. 1998, 72(10), 7992-8001.

Sausville, E.A. et al., "Contributions of human tumor xenografts to anticancer drug development,"Cancer Research, 2006, 66, 3351-3354.

Shao-Chieh, C. et al., "4-Alkylamino-3-Bromo-N-Alkyl-1,8-Naphthalimides; New Photochemically Activatible Antiviral Compounds," Bioorg Med Chem Letts, 1993, 3(4), 555-556.

Snipes et al., "Inactivation of Lipid-Containing Viruses by Hydrophobic Photosensitizers and Near-Ultraviolet Radiation," Photochemistry and Photobiology, Oxford, Jan. 1, 1979, 29(4), 785-790.

Teichert et al., "Treatment of oral candidiasis with mehtylene blue-mediated photodynamic therapy in an immunodeficient murine model," Oral Medicine, Oral Pathology, Oral Radiology & Endodontics, Feb. 2002, 93(2), 155-160.

Ugolini S, et al., HIV-1 attachment: another look. Trends Microbiol. Apr. 1999;7(4):144-9.

Volsky, D.J., "Fusion of human immunodeficiency virus type 1 (HIV-1) with human cells as measured by membrane fluorescence dequenching (DQ) method: Roles of HIV-cell fusion in AIDS pathogenesis" in Horizons in Membrane Biotechnology, 1990, Wiley-Liss, New York, pp. 179-198.

Vzorov, A.N. et al., "Inactivation of human immunodeficiency virus type 1 by porphyrins," Antimicrob Agents Chemother., Dec. 2002, 46(12), 3917-25.

Wallis, C. et al., "Influenza Vaccine Prepared by Photodynamic Inactivation of Virus," Journal of Immunology, Nov. 1963, 91, 677-682.

Weissenhorn W, et al., Atomic structure of the ectodomain from HIV-1 gp41. Nature. May 22, 1997;387(6631):426-30.

Wild C, et al., A synthetic peptide from HIV-1 gp41 is a potent inhibitor of virus-mediated cell-cell fusion. AIDS Res Hum Retroviruses. Nov. 1993;9(11):1051-3.

* cited by examiner

A

Vsc

B

| 200 nm

| 200 nm

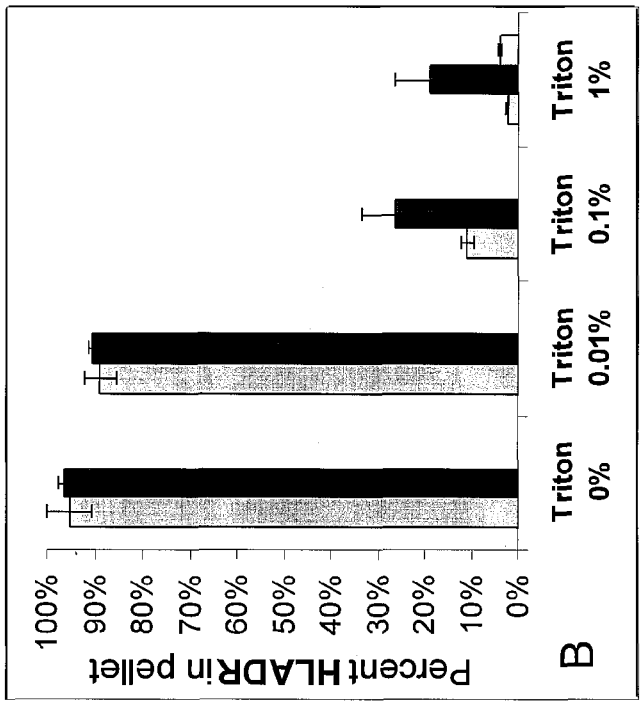
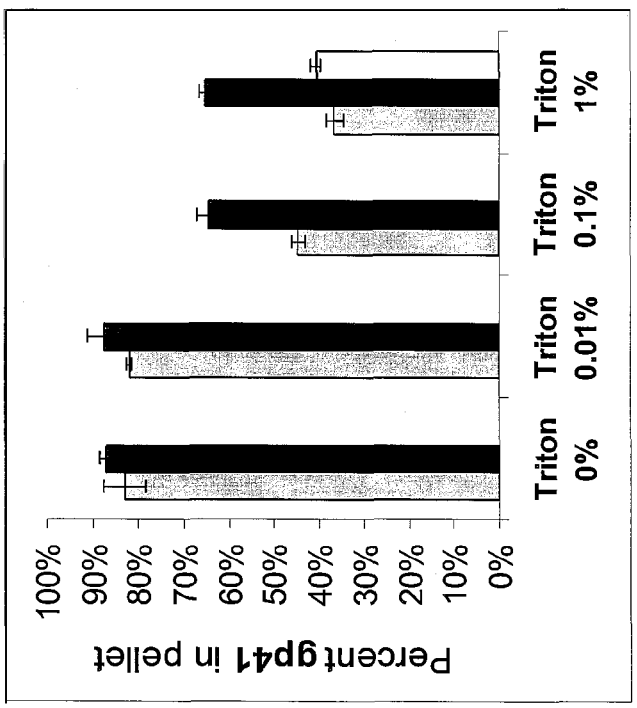
FIG. 9B
FIG. 9A

CELLULAR AND VIRAL INACTIVATION

CROSS REFERENCE TO RELATED APPLICATIONS

This application is a continuation-in-part of PCT/US2009/000623, filed Jan. 30, 2009, which claims the benefit of U.S. Provisional Application Ser. No. 61/025,424, filed Feb. 1, 2008 and U.S. Provisional Application Ser. No. 61/088,294, filed Aug. 12, 2008, the entireties of which are incorporated herein.

This application is also a continuation-in-part of U.S. application Ser. No. 11/525,250, filed Sep. 21, 2006, now U.S. Pat No. 8,268,602, which is a continuation of PCT/US2005/09559, filed Mar. 22, 2005, which claims the benefit of U.S. Provisional Application No. 60/555,268, filed Mar. 22, 2004, the entireties of which are incorporated herein

GOVERNMENT FUNDING

The inventions described herein were developed with support from the National Institutes of Health. The U.S. government has certain rights in the inventions.

TECHNICAL FIELD

The invention is related to methods for inactivation of viruses, in particular enveloped viruses, as well as parasites and tumor cells. The inactivated agents can be used as vaccines against the diseases caused by such viruses, parasites, and tumor cells. The inactivated agents can also be used as reagents in experimental procedures that require inactivated particles, for example, procedures that require inactivated viral particles that retain functional surface proteins. The inactivation methods preserve the integrity of structural and conformational features of the agents; hence, the immunogenicity of the agents, as a whole, is maintained and can be safely used for vaccination without the threat of infection.

BACKGROUND

Vaccination against pathogens has been one of the major accomplishments of medicine over the past century. While effective vaccines have been developed for a large number of diseases, development of safe and effective vaccines for a number of other diseases remains problematic. For example, the use of inactivated or killed microbial agents as a vaccine, although generally safe, will not always be effective if the immunogenic characteristics of the agent are altered. Indeed, the preferential degradation of certain antigens on the inactivated microorganisms might produce a weak or poorly targeted immune response that permits a pathological course when the host is later exposed to the live microorganism. In addition, while the preparation of live attenuated microbial agents as vaccines will often provide improved immunologic reactivity, use of such live attenuated microbial agents has an increased risk that the vaccine itself will be infectious. Such live attenuated vaccines can be infectious, for example, if mutation or reversion occurs, because the organism may be able to propagate and provide a reservoir for future infection.

Thus, one must often choose between improved effectiveness and greater degree of safety when selecting between the viral inactivation and viral attenuation techniques for vaccine preparation. The choice is particularly difficult when the virus is resistant to inactivation and requires rigorous inactivation conditions that are likely to degrade the antigenic characteristics.

Therefore improved methods for inactivating viruses are desirable, where the methods are capable of completely inactivating viruses without causing substantial degradation of the antigenic structure of these viruses. In particular, the inactivated viruses should be useful as vaccines and free from adverse side effects at the time of administration as well as upon subsequent challenge with the live infectious agent.

It is also desirable to provide improved methods for inactivating agents such as bacteria, cancer cells, and other cell types, where the methods are capable of inactivating these agents without causing substantial degradation of the antigenic structure of the agents. In particular, the inactivated agents should be useful as vaccines and free from adverse side effects at the time of administration, as well as upon subsequent challenge with the live agent.

SUMMARY

The present invention is directed to methods for inactivating a viral population comprising (a) contacting the viral population with a compound of formula I or II:

X—Ar—X      I

X—Ar      II wherein Ar is a hydrophobic moiety that can have one or more hydrogen, halide or alkyl substituents; and each X is separately a photoactivable group; (b) exposing the mixture to irradiation to crosslink viral proteins and generate a photocrosslinked viral preparation; and (c) removing lipids from viral membranes before or after steps (a) and (b) by extracting the photocrosslinked viral preparation with a detergent, to thereby inactivate a viral population. Compositions and vaccines comprising viral preparations prepared according to the described methods are also included within the scope of the invention. Methods of inhibiting viral infections comprising the described vaccines and compositions are also described.

BRIEF DESCRIPTION OF THE DRAWINGS

FIG. 2A-B shows transmission electron microscopic (TEM) images of HIV-1 (MN)/H9 Clone 4 virions before (FIG. 2A) and after (FIG. 2B) crosslinking using 1,5-diazidonaphthalene and UV irradiation for 15 minutes. V=virion, Vsc=microvesicle.

FIG. 9A-B shows that crosslinking HIV-1 MN virus preparations creates a detergent resistant fraction of virus as detected by an increase in the sedimented fraction after detergent treatment. The percentage in pellet was calculated as: % in pellet=(pellet integration)/(pellet integration+supernatant integration), where integrations of the lanes were taken on the Western blots using Odyssey IR imaging software. p24 data are the result of one experiment and the gp41 data are combined data from two completely separate experiments (error bars=standard deviation between the two experiments). SDS-PAGE and Western blotting of the supernatant and pellet were performed in the same fashion as described for FIG. 5.

FIG. 10A shows the percent p24 protein in the pellet after crosslinking and detergent-treatment of viral preparations, while FIG. 10B shows the percent gp41 protein in the pellet after crosslinking and detergent-treatment of viral preparations. The designation "main spot" indicates that integrations were done of only the main protein band (either gp41 or p24) for all samples, while the designation "entire lane" indicates that integration were performed for the entire lane for each sample. Percent in pellet was calculated as: % in pellet=(pellet integration)/(pellet integration+supernatant integration).

DETAILED DESCRIPTION OF ILLUSTRATIVE EMBODIMENTS

Figure 1:
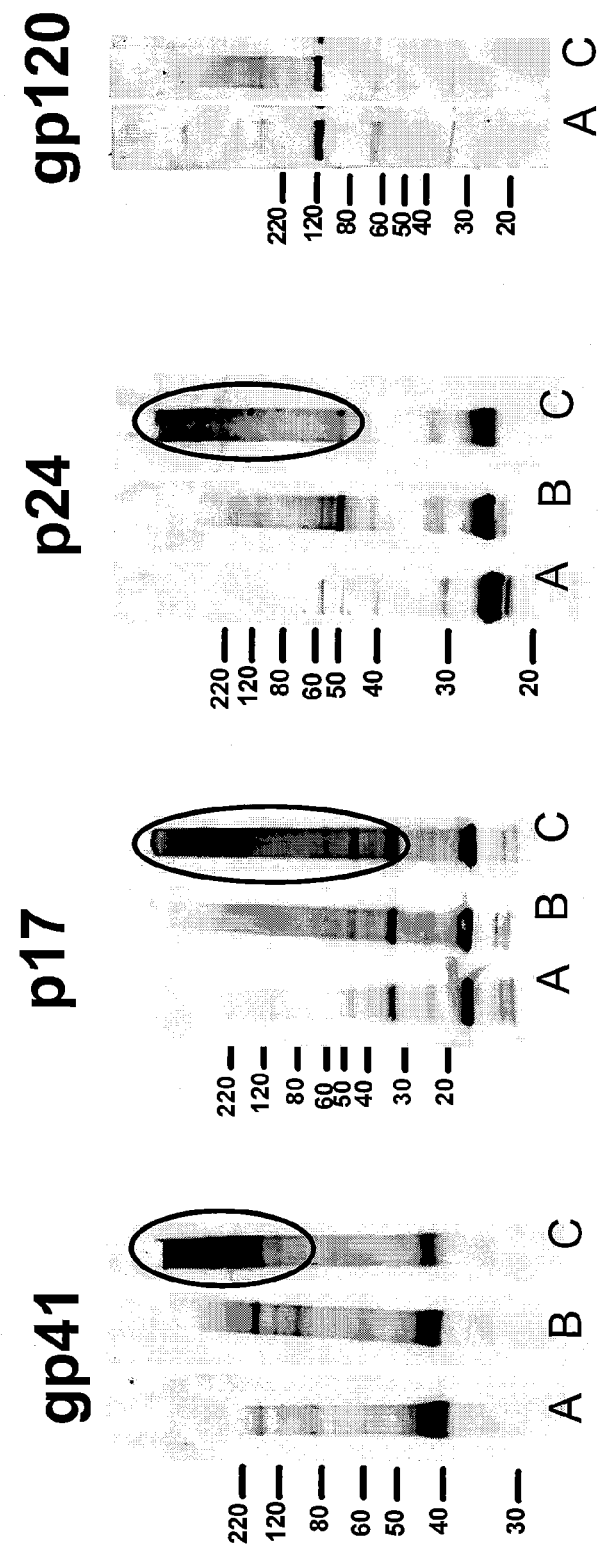
FIG. 1 illustrates crosslinking of transmembrane and capsid proteins after treatment of HIV-1 MN virions with 1,5-diazidonaphthalene (DAN), as shown by Western blot analyses using the indicated monoclonal antibodies (i.e., anti-gp41, anti-p24, anti-HLADR, anti-p17 and anti-gp120 antibodies). Thus, some of the gp41, p24, p17 and gp120 proteins from crosslinked viral preparations were detected in the high molecular weight range (circled portions) rather than as the lower molecular weight proteins observed for control (untreated) viral samples. Crosslinking conditions: DAN in DMSO (8.69 mM) was added to 0.5 mg HIV-1 MN total protein per ml, to yield a final concentration of 100 micromolar DAN. The mixture was then irradiated with UV for 15 minutes to crosslink the viral proteins. Controls are 0.5 mg/mL HIV-1 MN without any DAN or UV treatment.

The invention involves methods for inactivating viruses that include treatment of the virus with a compound which, after light activation, results in the covalent chemical crosslinking of adjacent proteins, primarily those located in the viral membrane. The method optionally includes detergent treatment, which effectively eliminates any residual active viruses, while preserving detergent-insoluble antigenic determinants of the crosslinked virions.

Currently available chemical treatments aimed at the inactivation of viruses are inherently susceptible to a low, but nontrivial, chance of residual infectivity. This is likely due to virions that either reside in a protected micro environment (e.g. inside a clump of viruses) or virions that have simply not had sufficient contact with the inactivating agent (due, e.g., to inadequate mixing).

However, the orthogonal inactivation methods described in this application strongly mitigate against the possibility of residual infectivity. Virions that have been inactivated by the chemical crosslinking step described herein are resistant to solubilization by treatment with detergents (e.g. Triton X-100) because the crosslinking not only helps to inactivate the virus but also helps stabilize the viral structure. Treatment of live viruses with detergents inactivates those viruses because the viruses are simply solubilized into their constituent parts. Inactivation by detergent treatment is therefore quite effective, but generally has the major disadvantage of eliminating the particulate structure of the virus and the native conformation of the constituent viral proteins. Accordingly, detergent treatment alone generally destroys the viral structures needed for effective immunization against the virus.

The inactivation method of the invention takes advantage of the detergent resistant nature of the crosslinked virions. Virus particles that somehow escape the crosslinking inactivation step, or are inadequately crosslinked, are highly vulnerable and susceptible to detergent solubilization. Thus, any virus particles that escape crosslinking, or are inadequately crosslinked, are eliminated by the subsequent detergent treatment. However, when the crosslinking step is effective, it results in detergent insoluble virions and antigenic fragments of the original virion structures, which still retain native conformation structures and viral epitopal structures important for generating an effective immune response against the virus.

There is also a third component of the method of the invention that contributes to viral inactivation, the UV irradiation step. UV irradiation not only helps crosslink proteins by activating the hydrophobic crosslinker, but is also an effective and widely used viricide that works by damaging viral nucleic acids. Thus, the UV irradiation step required to activate the chemical crosslinker also inactivates virions by two mechanisms—crosslinking and nucleic acid damage.

In summary, the orthogonal inactivation method of the invention inactivates viruses chemically by crosslinking constituent proteins and by damaging viral nucleic acids using UV light. Particles that somehow avoid crosslinking are solubilized by detergent treatment, resulting in inactivated viral preparations that are free of residual infectivity.

One aspect of the invention is therefore a method for inactivating a viral population comprising: (a) contacting the viral population with a hydrophobic crosslinker to generate a mixture of viral particles and the hydrophobic crosslinker; (b) exposing the mixture to light (e.g., ultraviolet) irradiation to crosslink viral membrane proteins to generate a photocrosslinked viral preparation; and (c) removing lipids from viral membranes by extracting the photocrosslinked viral preparation with a detergent, to thereby inactivate a viral population.

According to the invention, treatment of tumor cells with a photoactivatable hydrophobic compound of the invention blocks cell division and colony formation with substantially no detectable damage to the structural integrity of the cells. Moreover, using the methods described herein, viruses, bacteria, and parasites are completely inactivated when treated with appropriate concentrations of such photoactivatable hydrophobic compounds, which preferably crosslink membrane proteins when activated by light, in particular ultraviolet light. Minor, generally insubstantial changes in the structural integrity of the particles were observed. Modified viral particles of the invention reacted with monoclonal antibodies directed against selected viral proteins and the inactivated viruses bound to their target cells. Viral fusion was, however, impaired by use of the present methods.

Optionally, the viral membrane lipids can be removed using a detergent. Treatment with detergent also eliminates any virions that may have escaped inactivation by crosslinking. This regimen not only inactivates the virus but also preserves native viral epitopes so that animals can develop an effective immune response against the virus that mitigates against subsequent infection when the animal is later exposed to live viruses. While any one of three inactivation steps (crosslinking, UV irradiation and detergent treatment) will lead to substantial viral inactivation, the combination of these three steps ensures that the viral preparation is as safe as technically possible for human and mammalian/avian administration whilst maintaining optimal immunogenicity.

Hence, the invention provides new methods for inactivating viruses, bacteria, parasites, and tumor cells. These inactivated agents can be used in compositions to stimulate an immune response against active viruses, bacteria, parasites, and tumor cells. In other embodiments, the invention provides vaccines to prevent the diseases caused by such viruses, bacteria, parasites, and tumor cells.

Crosslinking Agents

According to the invention, a photoactivatable crosslinker is used that is soluble within membranes and/or can at least partially pass through viral membranes. In general, the photoactivatable crosslinker inactivates viruses without adversely affecting native antigenic epitopes present on the surface of the virus. Viruses treated with crosslinker agents according to the methods of the invention are inactivated and are noninfectious, for example, because the viruses are no longer capable of fusing with animal host cells. The crosslinking agent employed in the methods of the invention are generally hydrophobic crosslinking agents. Moreover, the crosslinking agents of the invention crosslink viral proteins, lipids and other viral structures after they are photoactivated.

In some embodiments, the crosslinking agents form covalent bonds or crosslinks to and/or between viral proteins. In other embodiments, the crosslinking agents promote detergent resistance by linking the hydrophobic crosslinking agent to viral proteins and causing those viral proteins to aggregate.

Hence, the crosslinking agent can act through non-covalent aggregation, hydrophobic labeling, and/or by promoting protein aggregation, as well as by covalent crosslinking.

Hydrophobic crosslinkers of the invention include those of formula I, IA, and/or II:

wherein:
Ar is a hydrophobic moiety that can have one or more hydrogen, halide or alkyl substituents; and
each X is separately a photoactivatable group;
Y can be hydrogen or a photactivatable group.

The Ar group is a hydrophobic moiety preferentially partitions out of an aqueous environment and into a cellular or viral membrane. The Ar group preferably comprises one, two, three or more rings that are either fused together or linked together via one or more alkylene, alkenylene, diazene, or carbonyl moieties. The rings can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art. The Ar ring(s) can be substituted with one or more hydrogen, halide or alkyl substituents. Examples of hydrophobic rings that can be employed in the Ar groups include phenyl, naphthyl, and anthracenyl moieties. The Ar group can also include linear, branched, cyclic, and acyclic hydrocarbons and combinations thereof. For example, the Ar group can be a fatty acid, alkyl, adamantine, pyrene, phenanthracene, and the like.

The photoactivatable group can, for example, be an azide (i.e., $N_3$ generating a nitrene intermediate), an diazirine (i.e., a three-membered nitrogen ring generating a carbene intermediate) or a carbonyl flanked by two aryl rings (e.g., benzophenone generating a radical intermediate). In one embodiment of the invention, the X and/or Y reactive groups are separately azido (—$N_3$), halo (Cl, Br or I), halo lower alkyl (e.g. $CF_3$), diazirene, azidocarbonyloxy (—O—CO—$N_3$), haloacetamide (—NH—(C=O)—$CH_2$—Z), where Z is Cl, Br or I. Alternatively, the reactive groups are separately amine, maleimide, isocyanato (—N=C=O), isothiocyanato (—N=C=S), acyl halide, succinimidyl ester, or sulfosuccinimidyl ester. In another embodiment, the reactive groups are carboxylic acid (COOH), or derivatives of a carboxylic acid. An appropriate derivative of a carboxylic acid includes an alkali or alkaline earth metal salt of carboxylic acid. Alternatively, the reactive groups are reactive derivatives of a carboxylic acid (—COOR), where the reactive group R is one that activates the carbonyl group of —COOR toward nucleophilic displacement. In particular, R is any group that activates the carbonyl towards nucleophilic displacement without being incorporated into the final displacement product. Examples of COOR groups include esters of phenol or naphtol that are further substituted by at least one strong electron withdrawing group, or carboxylic acid activated by carbodiimide, or constitute acyl chloride, azido, succinimidyl or sulfosuccinimidyl ester. Additional charged groups include, among others, sulfonyl halides, sulfonyl azides, alcohols, thiols, semicarbazides, hydrazines or hydroxylamines.

Examples of hydrophobic agents that can be used in the invention include the following:

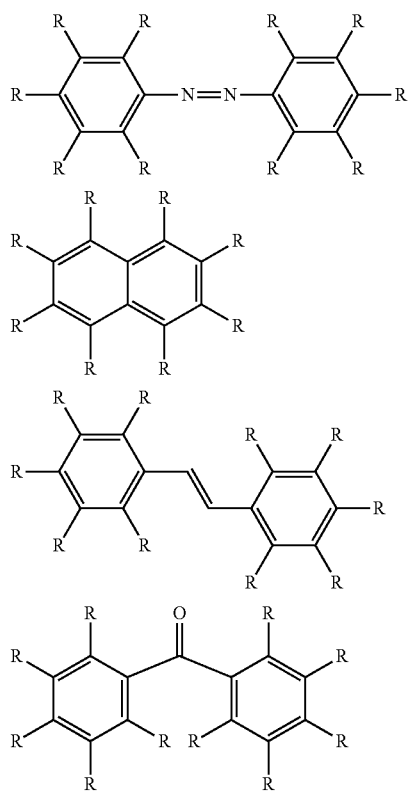

wherein each R is independently hydrogen, halide, lower alkyl or a photoactivatable group, provided that there is at least one photoactivatable group that produces a reactive intermediate upon photoactivation.

Further examples of compounds that can be used in the invention include the following:

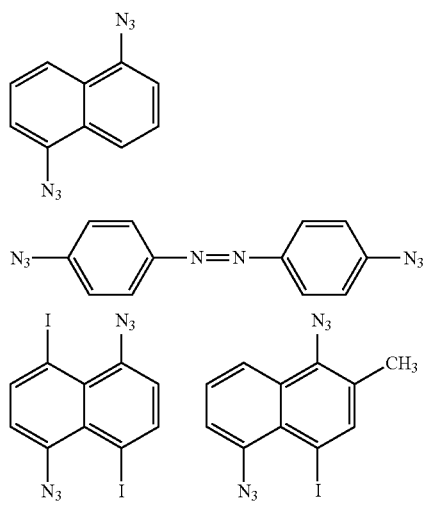

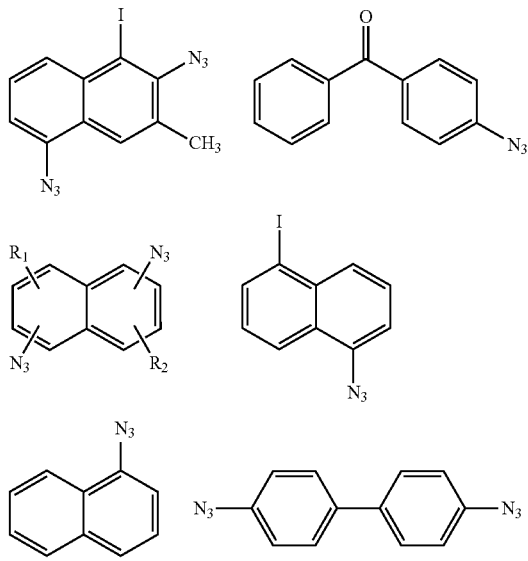

wherein $R_1$ and $R_2$ are separately H, halide or lower alkyl. In some embodiments, $R_1$ and $R_2$ are separately H, iodide (I) or methyl ($CH_3$).

Other preferred compounds for use in the invention include:

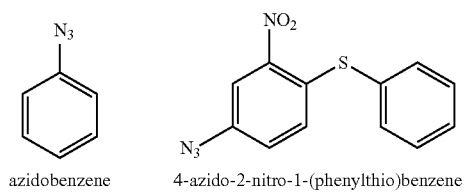

azidobenzene      4-azido-2-nitro-1-(phenylthio)benzene

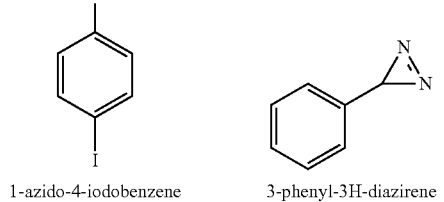

1-azido-4-iodobenzene      3-phenyl-3H-diazirene

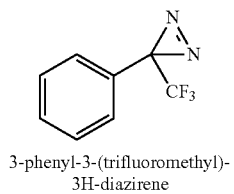

3-phenyl-3-(trifluoromethyl)-
3H-diazirene

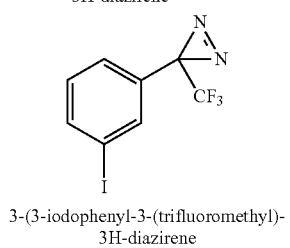

3-(3-iodophenyl-3-(trifluoromethyl)-
3H-diazirene

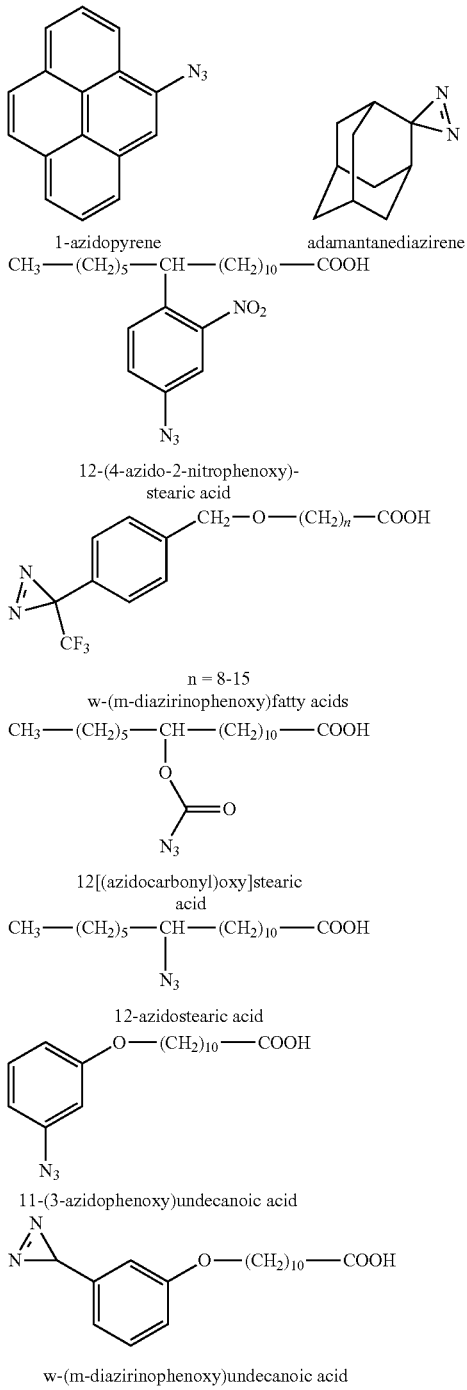

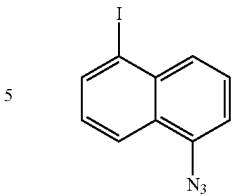

In one embodiment, 1,5-iodonaphthyl azide (INA) is employed as a photoactivatable hydrophobic compound. INA is a non toxic hydrophobic compound. The structure for 1,5-iodonaphthyl azide (INA) is provided below. See also, Bercovici and Gitler 1978, Biochemistry, 17: 1484-89.

Upon exposure to cells, including viruses, bacteria, parasites, and tumor cells, the compounds of the invention penetrate into biological membrane bilayers and are active and accumulate in the membrane and/or in the interior of virus, bacteria, parasite, or tumor cell.

The compounds of the invention are light sensitive. Upon irradiation with ultraviolet light (e.g., 300 to 400 nm or 320 nm to 400 nm) a reactive derivative is generated that binds to and optionally crosslinks membrane proteins deep in the lipid bilayer and/or within the viral particle, bacteria, or tumor cell. This process inactivates and optionally crosslinks membrane proteins embedded in the membrane while maintaining the integrity of the proteins that protrude from the extracellular surface of the membrane.

In addition, the compounds of the invention may be used for inactivation of viruses, bacteria, parasites, and tumor cells using visible light. However, when visible light is used, a photosensitizer chromophore is needed. This photosensitizer chromophore has an absorption maximum in the visible light range and may photosensitize the photoactivatable hydrophobic crosslinking compounds of the invention. In general, the photosensitizer chromophores have absorption maxima in the range of about 450 to about 525 nm or about 600 to about 700 nm. The photosensitizer chromophore can be a porphyrin, chlorin, bacteriochlorin, purpurin, phthalocyanine, naphthalocyanine, merocyanines, carbocyanine, texaphyrin, non-tetrapyrrole, or other photosensitizer known to one of skill in the art. Specific examples of photosensitizer chromophores include fluorescein, eosin, bodipy, nitro-benzo-diazol (NBD), erythrosine, acridine orange, doxorubicin, rhodamine 123, picoerythrin and the like.

Treatment with Compounds of the Invention

As provided herein, viruses, bacteria, parasite, and tumor cells can be inactivated by exposure to compounds of the invention. While any of the compounds described herein can be employed, in some embodiments, the compound is 1,5-diazidonaphthalene (DAN), 1-azido-5-iodonaphthalene (INA) 1-azidonaphthalene (AzNAP), 4,4'-diazidobiphenyl (AzBIPH) or a related compound. After contacting compound with the virus, bacteria, parasite or tumor cell to form a mixture thereof, the mixture is exposed to light. If the virus, bacteria, parasite or tumor cell is contacted with just the photoactivatable hydrophobic compound, ultraviolet light is used. If the virus, bacteria, parasite or tumor cell is contacted with both the compound and a photosensitizer chromophore that absorbs visible light, then visible light may be used. Exposure to ultraviolet light directly photoactivates the photoactivatable compound of the invention within the virus, bacteria, parasite or tumor cell, including within the interior of the virus, bacteria, parasite or tumor cell and within virus, bacteria, parasite or tumor cell membranes. Exposure to visible light first photoactivates the photosensitizer chromophore, which then activates or photosensitizes the photoactivatable compound within the virus, bacteria, parasite or tumor cell. In either case, a reactive derivative of the photoactivatable compound is generated that binds to proteins within the virus, bacteria, parasite or tumor cell and/or within virus, bacteria, parasite or tumor cell membranes. This process causes specific inactivation of virus, bacteria, parasite or tumor cell proteins, including those within the virus, bacteria, parasite or tumor cell and virus, bacteria, parasite or tumor cell proteins embedded in the membrane. In general, the structures of proteins that protrude from the membrane are preserved in their native conformation.

Prior to exposure to a compound of the invention, viruses can be washed to remove media, waste and other materials that might reduce partitioning of the photoactivatable compound into viral membranes. For example, the viruses can be washed in serum-free media, saline, phosphate-buffered saline or other solutions selected by one of skill in the art.

The amount of photoactivatable compound used to inactivate a virus, bacteria, parasite or tumor cell can vary and may depend upon the type of virus, bacteria, parasite or tumor cell, as well as the conditions under which the photoactivatable compound is reacted with the virus, bacteria, parasite or tumor cell. For example, if competing hydrophobic molecules are present in the media, then larger amounts of the photoactivatable compound may be needed.

In some embodiments, the concentration of the photoactivatable compound of the invention employed in a mixture with a virus, bacteria, parasite or tumor cell can vary from about 0.1 micromolar to about 1 millimolar, or from about 1 micromolar to about 700 micromolar, or from about 10 micromolar to about 500 micromolar, or from about 20 micromolar to about 400 micromolar, or from about 30 micromolar to about 300 micromolar, or from about 50 micromolar to about 250 micromolar.

When expressed as a ratio of the amount of photoactivatable compound employed per amount of virus, bacteria, parasite or tumor cell protein, this ratio can vary from about 0.1 micrograms photoactivatable compound per milligram of protein to about 500 micrograms photoactivatable compound per milligram of protein. In other embodiments, the amount of photoactivatable compound used can vary from about 0.5 to about 200, or about 1 to about 150, or about 2 to about 125, or about 3 to about 100 micrograms photoactivatable crosslinker per milligram of protein.

The amount of photosensitizer chromophore used to activate the photoactivatable compound can also vary and depends to some extent on the photosensitizer chromophore used, the photoactivatable compound employed and the type of virus, bacteria, parasite or tumor cell. For example, about 0.01 mg/ml to about 50 mg/ml photosensitizer chromophore may be used, or about 0.1 mg/ml to about 5 mg/ml photosensitizer chromophore may be used, or about 0.3 mg/ml to about 1 mg/ml photosensitizer chromophore may be used.

Exposure to Light

After forming a mixture of the virus, bacteria, parasite or tumor cell with a photoactivatable compound of the invention, the mixture is exposed to light for a time and under conditions sufficient for generating a reactive derivative that can bind to membrane proteins within the lipid bilayer. In some embodiments, the mixture is exposed to light for a time and under conditions sufficient for generative a reactive derivative that can crosslink viral proteins.

The wavelength of light employed for generating a reactive derivative can vary and depends to some extent upon the photoactivatable hydrophobic crosslinker employed.

Thus, in some instances, the appropriate wavelength of light used for generating the reactive derivative is an ultraviolet wavelength. For example, the wavelength may be about 254 nm to about 400 nm. In some embodiments, the wavelength is about 254 nm to about 380 nm. In other embodiments, the wavelength is about 280 to about 380 nm. In further embodiments, the wavelength is about 320 nm to about 380 nm. In still further embodiments, the wavelength is about 340 nm to about 360 nm. In other embodiments, the wavelength can be about 320 nm to about 400 nm. In some embodiments, the wavelength is about 330 nm to about 380 nm. In other embodiments, the wavelength is about 340 nm to about 360 nm.

Visible light of an appropriate wavelength may also be used when a photosensitizer chromophore is employed that is incubated with or is localized in the vicinity of the photoactivatable compound of the invention. In general, the photosensitizer chromophores have absorption maxima in the range of about 450 to about 525 nm or about 600 to about 700 nm.

Light for photoactivation of the photosensitizer chromophore or the hydrophobic derivative can be from various light sources. For example, suitable light sources include broadband conventional light sources, broad arrays of LEDs, laser beams, defocused laser beams, optical fiber devices and transillumination. The light can be filtered to eliminate certain types or wavelengths of light. Hence, the light can be filtered to provide ultraviolet light (e.g., 300 to 400 nm), or visible light of selected wavelengths (e.g., 450 to 525 nm or 600 to 700 nm). The light can also be filtered to reduce heat production, for example, by passing the light through water.

Different light sources of different powers can be used: an incandescent light source like tungsten or halogen lamps will have a power range from 100-200 Watt. Mercury or Xenon light sources have a power range between 100-1000 Watt. A laser source will have the power range of 1-10 Watts. When visible light is used in the presence of a photosensitizer chromophore, the tungsten, halogen, Mercury and Xenon light sources should be equipped with optical filters or a monochromator that will filter out all wavelengths below 400 nm. When a laser is used, the appropriate wavelength line of 400 nm or higher should be used depending on the photosensitizer chromophore employed.

Regardless of the light source the intensities of light on the target sample should be in the range of 1-50 milliwatt/cm$^2$/min depending on the nature of the sample and the area irradiated.

Light exposure times can vary. For example, one of skill in the art may choose to expose a mixture of a photosensitizer chromophore and/or a photoactivatable compound and a virus, bacteria, parasite, or tumor cell to a light source for about 1 second to about 20 minutes or to about 30 minutes, or about 30 seconds to about 25 minutes, or about 3 seconds to about 15 minutes, or about 1 minute to about 22 minutes, or about 2 minutes to about 20 minutes, or about 3 minutes to about 20 minutes, or about 5 minutes to about 20 minutes or about 5 seconds to about 10 minutes, or about 7 seconds to about 7 minutes, or about 30 seconds to about 5 minutes. In some embodiments, the light exposure is more than about 2 minutes and up to about 30 minutes. A series of short (e.g., about 1 second or about 10 seconds to about 60 seconds) or longer (e.g., about 20 to about 60 seconds) light exposures can also be employed. When a laser is used, substantially shorter exposure times are typically used, for example, about 0.1 second to about 5 seconds, or about 0.5 seconds to about 3 seconds.

As is appreciated by one of skill in the art, the exposure time can vary depending on the wattage of the light employed. Viral supernatant isolated from infected cells or viruses purified and concentrated (e.g., by centrifugation) can be treated with a selected photoactivatable compounds of the invention and/or a photosensitizer chromophore and then exposed to light. The exposure time and wattage of the light employed may vary depending on the thickness and material used for containing the virus (e.g., a centrifuge tube or a microfuge tube). For example, less exposure may be needed for viral suspensions in narrow containers because the light will have a shorter pathlength. Thus, longer exposure times will be needed for larger flasks than for smaller microfuge tubes. Hence, some variation and deviation from the ranges provided herein is possible without deviating from the scope of the invention.

Either cultures or plates of viruses, bacteria, parasites or tumor cells can be treated with a selected photoactivatable compound and/or a photosensitizer chromophore and then exposed to light. The exposure time and wattage of the light employed may be different if a culture or plate of viruses/cells is employed. For example, less exposure may be needed for plated viruses/cells than for viruses/cells cultured in suspension because the depth of the culture may influence the degree to which the light penetrates the culture. Hence, some variation and deviation from the ranges provided herein is possible without deviating from the scope of the invention.

As described in more detail herein, 1,5-diazidonaphthalene has been shown by the inventors to penetrate into the inner most segments of membrane bilayers and accumulate within the virus and/or within the membrane(s) of the virus. As shown herein, upon irradiation of the virus with ultraviolet light (e.g., 320-400 nm), 1,5-diazidonaphthalene is photoactivated to generate a reactive derivative that binds to proteins within the virus, bacteria, parasite, or tumor cell and/or to membrane proteins within the lipid bilayer. This process causes specific inactivation of proteins within the virus and/or within the viral membrane, while maintaining the structure of the virus. Moreover, the crosslinking step of the inventive methods help preserve the structural integrity of viral particle so proteins that normally protrude from the membrane are still displayed in their native conformation and are readily recognized by the mammalian or avian immune system.

Detergent Treatment

Detergents that can be used in the inactivation methods of the invention include beta-cyclodextrin, methyl-beta-cyclodextrin, polyoxyethylene derivatives of a fatty acid, partial esters of anhydrous sorbitol such as Polysorbate 80 (e.g., Tween 80™, etc.) and Polysorbate 20 (e.g., Tween 20™, etc.); and nonionic oil bath rinsing agent such as oxyethylated alkylphenol (e.g., Triton X-100™, etc.). Examples include surfactants and detergents such as Zwitterionic detergents, Triton X-100, sodium dodecyl sulfate, and the like. The structure of Triton X-100 is as follows.

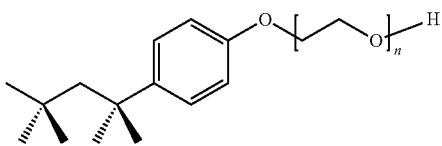

wherein n is an integer of 9 or 10.

Various amounts of detergent can be used for inactivating viruses. For example, viral suspensions can be treated with about 0.001% to about 10% detergent. In some embodiments, the detergent is used at a concentration of about 0.01% to about 3% detergent. As illustrated herein, viruses can be effectively treated after crosslinking using about 1% Triton X-100.

Viral preparations are exposed to the detergent for varying times. For example, viral preparations can be exposed to detergent for about 5 minutes to about 8 hours. In some embodiments the viral preparations are treated with detergent for about 10 minutes to about 180 minutes. In other embodiments, the viral preparations are treated with detergent for about 30 minutes to about 90 minutes.

The temperature used for detergent treatment can vary. However, one of skill in the art will generally select temperatures where the detergent solution is warm enough to be liquid and free-flowing (not viscous), yet not so hot that proteins become denatured. Thus temperatures of about 4° C. to about 42° C. can be used for detergent treatment of viral preparations. In some embodiments, the temperature is about 10° C. to about 40° C. or about 18° C. to about 38° C.

This detergent treatment step can be performed before or after the crosslinking step. However, when the detergent step is performed prior to crosslinking, only selected detergents can be used that do not destroy viral particles. Examples of detergents that do not destroy viral structures but that still remove lipids (e.g., cholesterol) from the viral membrane include beta-cyclodextrin and methyl-beta-cyclodextrin.

When the detergent step is performed after the crosslinking step, other detergents can be used, including those that would destroy viral particles if the crosslinking step were not performed. Examples of detergents that can be used include polyoxyethylene covalently linked to a fatty acid, polysorbate 80, polysorbate 20, oxyethylated alkylphenol or sodium dodecyl sulfate. In some embodiments, the detergent may be a compound of the formula:

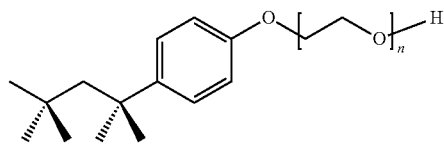

wherein n is an integer of 9 or 10.

Methods of Using the Inactivated Viruses, Bacteria, Parasites, and Tumor Cells

The invention provides a method that can inactivate viruses, bacteria, parasites, and tumor cells in such a way that they may safely be used as immunological compositions or vaccines to inhibit the disease they cause. The inactivation kills the virus, bacteria, parasite, or tumor cell in a manner that specifically maintains its structure and conformation. Hence, the structure of the inactivated virus, bacteria, parasite, or tumor cell is similar to that of the live virus, bacteria, parasite, or tumor cell. In this way, the immunogenicity of the virus, bacteria, parasite, or tumor cell is maintained and may be safely used to stimulate the immune system of a subject animal or patient. Similarly, the inactivated virus, bacteria, parasite, or tumor cell of the invention may be used for vaccination without causing disease or other negative side effects.

Studies have specifically illustrated that 1,5-diazidonaphthalene (DAN), 1-azido-5-iodonaphthalene (INA), 1-azidonaphthalene (AzNAP), and 4,4'-diazidobiphenyl (AzBIPH) can be used to inactivate live HIV.

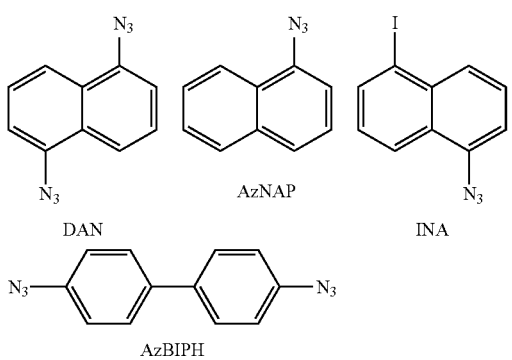

Figure 3:
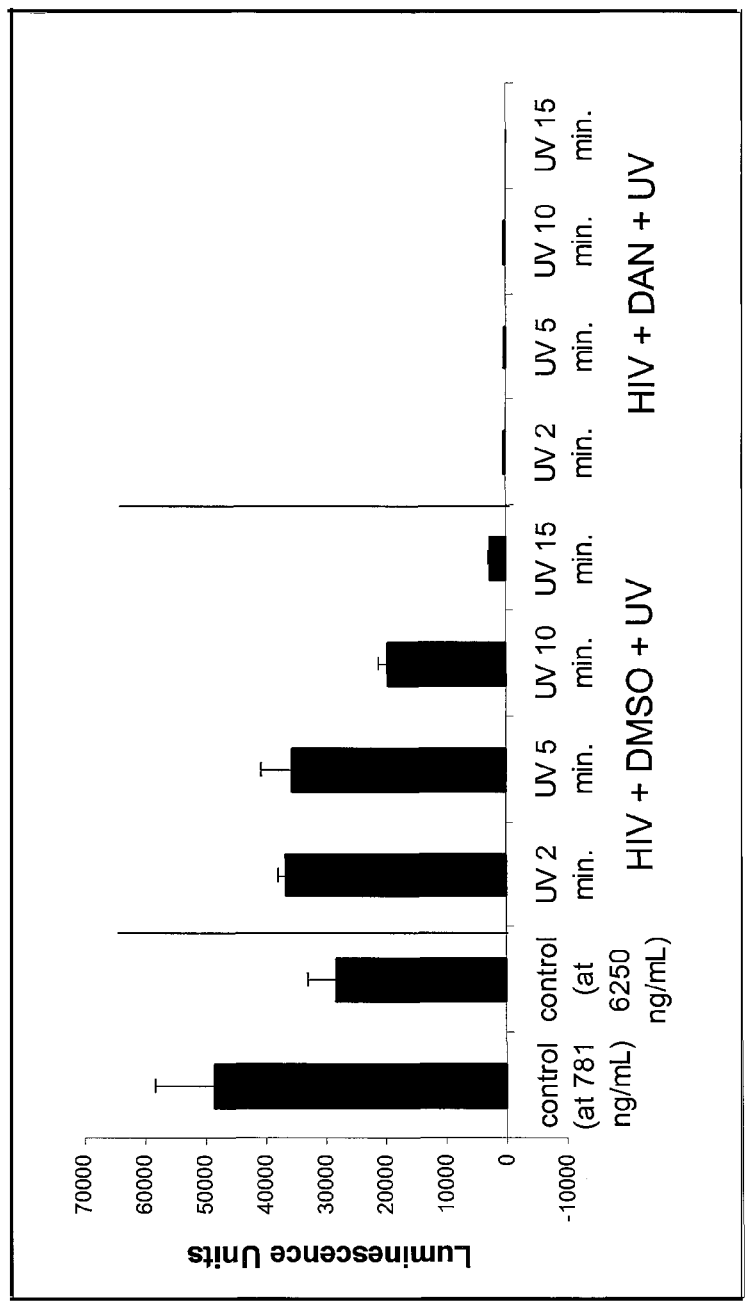
FIG. 3 illustrates that treatment of HIV-1 MN using DAN and UV irradiation for 2, 5, 10 or 15 minutes to crosslink viral membrane proteins causes significant reduction in viral infectivity as detected by a luciferase reporter gene assay. UV irradiation for increasing lengths of time led to significant reduction in viral infectivity. However, UV irradiation alone did not reduce infectivity to the same degree as UV plus crosslinking with DAN. Infectivity of the viral preparations, treated using methods described in Example 1, was measured by luminescence in TZM-bl cells after 24 hrs. The control samples shown are HIV loaded onto the assay plate at 781 ng/mL and 6250 ng/mL total protein. The higher concentration in the controls appears to have lower infectivity due to the cytotoxicity of the virus at higher concentrations. This higher concentration, 6250 ng/mL, was used for the rest of the samples. The samples labeled "HIV+DMSO+UV" show the infectivity of uncrosslinked HIV-1 MN samples containing 2% DMSO with UV treatment for the times specified. The samples labeled "HIV+DAN+UV" show the infectivity of crosslinked HIV-1 MN samples using 100 micromolar DAN with UV treatment for the times specified.
Figure 4:
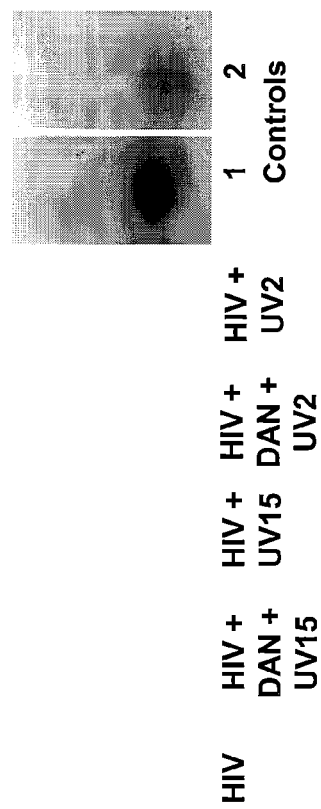
FIG. 4 illustrates that treatment of HIV with 1,5-diazidonaphthalene (DAN) using UV irradiation for 2 (UV2) or 15 (UV15) minutes to cross-link viral membrane proteins causes significant reduction in viral infectivity as detected by a polymerase chain reaction (PCR) assay for viral (gag) nucleic acids. Untreated HIV and HIV treated only with UV light for 2 minutes were still able to replicate gag nucleic acids at 21 days post-infection (see dark band at about 150 kilobase pairs). However, no such gag nucleic acids were detected 21 days post-infection when HIV were treated with DAN and UV light for either 2 or 15 minutes. Treatment of HIV with UV light alone for 15 minutes also led to undetectable levels of HIV gag nucleic acids. DNA was extracted from HIV-1 infected supT1 cells 21 days post-infection and viral replication was measured by PCR of gag sequences. The gag amplicon is the higher molecular weight band present in the lane labeled "HIV." The lane labeled "HIV" shows the amount of gag detected in uncrosslinked HIV-1 MN samples in PBS without UV treatment. The lane labeled "HIV+UV15" shows the amount of gag detected for HIV in PBS with 1% DMSO after irradiation with UV for 15 minutes (or 2 minutes for the lane labeled "HIV+UV2"). The lane labeled "HIV+DAN+UV15" shows the amount of gag detected for HIV treated with 100 μM of 1,5-diazidonaphthalene and then with UV irradiation for 15 minutes. The lane labeled "HIV+DAN+UV2" shows the infectivity of HIV treated with 100 μM 1,5-diazidonaphthalene and then with UV irradiation for 2 minutes. The lane labeled "Control 1" shows the amplification products of DNA extracted from uninfected sup T cells. The lane labeled "Control 2" shows a PCR assay performed without cellular/viral DNA (using primers only).
Figure 5:
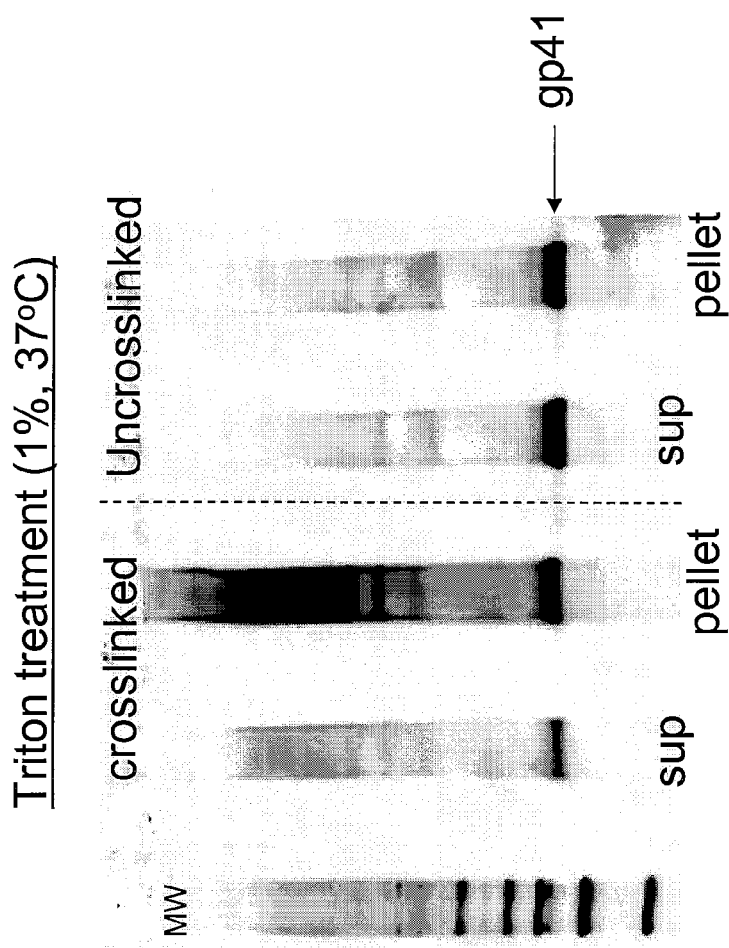
FIG. 5 illustrates that the amount of sedimented gp41 transmembrane protein increases when HIV is crosslinked prior to treatment with detergent (1% Triton X-100 at 37° C. for 1 hour) to inactivate viruses by removing viral membrane lipids. A western blot for gp41 is shown with crosslinked samples versus uncrosslinked controls. Similar results were obtained when HLADR and p24 were detected (not shown). "Sup"=supernatant above a sucrose cushion used during centrifugation, and "Pellet"=sedimented viral particles. HIV-1 MN was crosslinked using 100 μM of 1,5-diazidonaphthalene plus UV irradiation for 15 minutes, followed by treatment with 1% Triton X-100 at 37° C. for 1 hour. The HIV control was uncrosslinked virus subjected to the same detergent treatment. Both detergent-treated viral preparations were passed through a 23% sucrose cushion at 45,000 rpm for 35 minutes (Optima TLX Ultracentrifuge with a TLA 120.1 rotor) to separate crosslinked viral particles from viral proteins present in the supernatant.
Figures 10A, 10B:
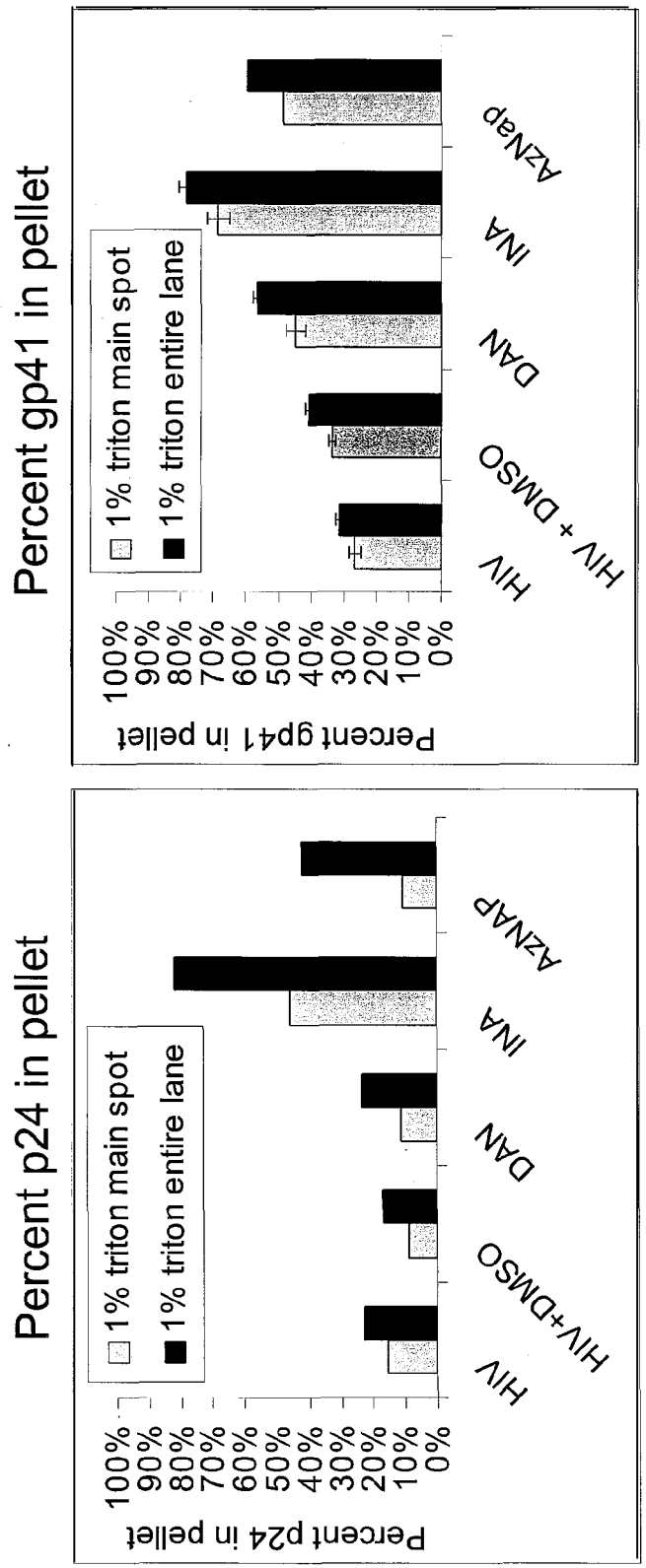
FIG. 10A-B illustrate that crosslinking of HIV-1 MN virus preparations creates a detergent resistant fraction of virus as detected by an increase in the sedimented fraction after detergent treatment.

For example, treatment with 1,5-diazidonaphthalene produced inactive viruses with no detectable infectivity (FIGS. 3 and 4) and with no significant change to their structural integrity (FIGS. 1 and 2). While the molecular weight of viral proteins may increase (due to crosslinking between proteins) such crosslinking did not affect the ability of these proteins to react with antibodies that are known to bind to HIV (FIGS. 1 and 5). However, the 1,5-diazidonaphthalene treatment impaired the ability of the virus to express virally encoded functions (FIG. 4). Viral growth in cells that normally would become infected was essentially eliminated (FIGS. 3 and 4). In addition, the crosslinking step maintained the structural integrity of portions of the viral particle during treatment with a detergent (e.g., Triton X-100) (FIGS. 5, 9 and 10). In particular, after crosslinking and treatment with Triton X-100, an increased amount of viral antigens were recovered by sedimentation when compared to the non-crosslinked controls. Such a detergent would normally dissolve viral lipids and dissociate viral proteins, leading to complete destruction of viral secondary and tertiary structures. Therefore, the fact that a greater number of viral antigens were recovered by sedimentation after detergent treatment, when compared to non-crosslinked controls, indicates that the crosslinking step helped preserve antigenic structures of the viral particle, rendering them detergent insoluble.

Figures 7A, 7B:
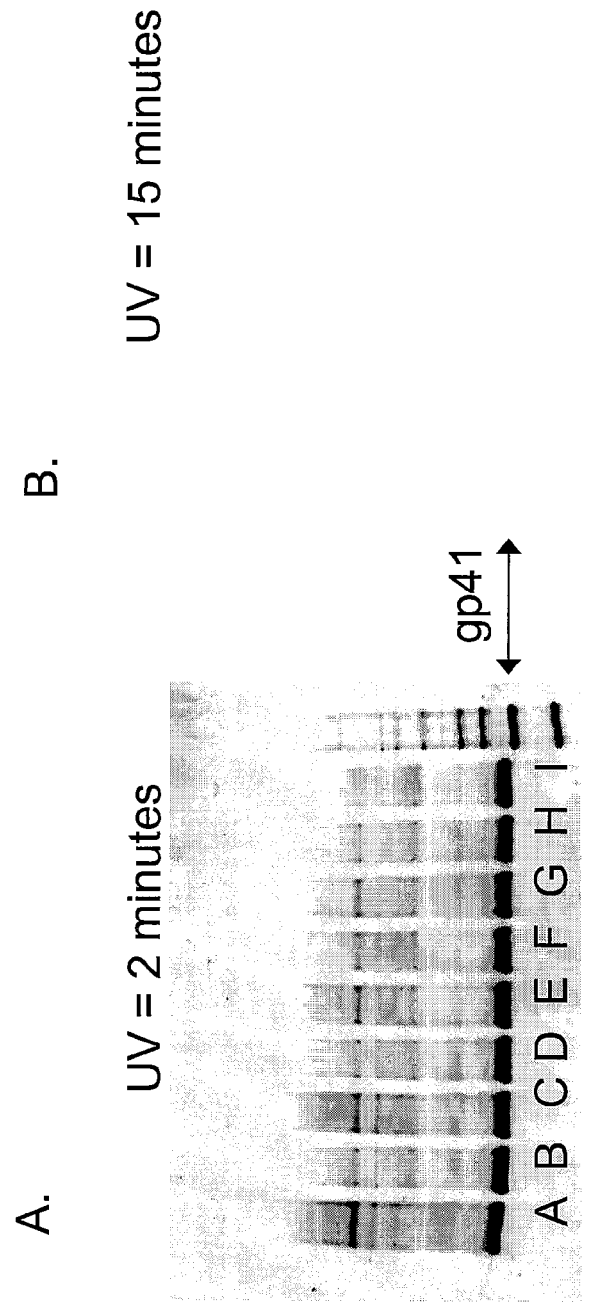
FIG. 7A-B show that a variety of crosslinking agents are useful for aggregating and/or crosslinking viral proteins. Solutions of HIV-1 virus were treated with chemical crosslinker or control, and then UV irradiated for either two minutes (FIG. 7A) or 15 minutes (FIG. 7B). In some cases, a filter was placed between the ultraviolet light source and the viral solution ("with filter") to filter out light of wavelength 360 nm. As shown for lanes B and D, somewhat less crosslinking is observed when the filter was employed. The viral protein in the various viral preparations were separated by SDS-PAGE run under reducing conditions, followed by blotting onto nitrocellulose and probing via Western analysis using anti-gp41, with AlexaFluor-conjugated secondary antibodies for IR readout and the Odyssey IR imaging system. The lanes contain HIV-1 treated as follows: (A) HIV+INA+ UV no filter; (B) HIV+INA+UV with filter; (C) HIV+DAN+ UV no filter; (D) HIV+DAN+UV with filter; (E) HIV+ AzNAP+UV no filter; (F) HIV+INAP+UV no filter; (G) HIV+DIN+UV no filter; (H) HIV+DMSO+UV no filter; (I) HIV control (no DMSO, no UV).
Figure 8:
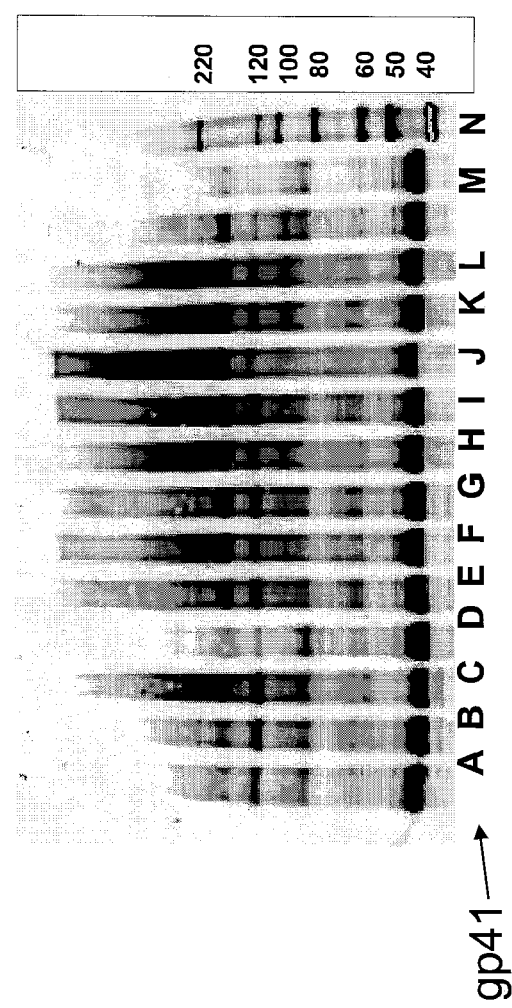
FIG. 8 illustrates that greater crosslinking/aggregation is observed after treatment with hydrophobic crosslinkers and UV irradiation for 15 minutes than observed for formalin-treated viral controls. Formalin treatments were done using concentrations comparable to those used in the preparation of formalin-inactivated virus vaccines. After crosslinking or for-malin treatment, the viral proteins were electrophoretically separated via SDS-PAGE, which was run under reducing conditions. The gel was blotted onto nitrocellulose and probed using standard Western blot procedures and anti-gp41 antibodies, with AlexaFluor-conjugated secondary antibodies for IR readout using the Odyssey IR imaging system. The lanes shown in FIG. 8 represent electrophoretically separated HIV-1 proteins from HIV-1 subjected to the following: (A) HIV+Formalin, 0.02% in PBS; (B) HIV+Formalin, 0.04% in PBS; (C) HIV+Formalin, 0.1% in PBS; (D) HIV+Formalin, 0.03% in Calcium Saline Buffer; (E) HIV+AzBIPH+UV 2 minutes; (F) HIV+INA+UV 2 minutes; (G) HIV+AzBIPH+ UV 15 minutes; (H) HIV+INA+UV 15 minutes; (I) HIV+ AzBIPH+UV 15 minutes; (J) HIV+INA+UV 15 minutes; (K) HIV+DAN+UV 15 minutes; (L) HIV+AzNAP+UV 15 minutes; (M) HIV+DMSO+UV 15 minutes; (N) HIV control (no DMSO, no UV).

INA and AzNAP also effectively crosslink HIV proteins upon UV irradiation, leading to protein aggregation (FIG. 7). Moreover, greater crosslinking/aggregation occurs after treatment with hydrophobic crosslinkers AzBIPH and INA followed by UV irradiation, than is observed when formalin is used (FIG. 8). Formalin treatments were done using concentrations comparable to those used in the preparation of formalin-inactivated virus vaccines. Table 1 shows that the crosslinking methods of the invention (e.g., using INA and DAN in that experiment) effectively eliminate HIV-1 infectivity as observed by using a highly sensitive 28-day infectivity assay. Accordingly, these results indicate that the hydrophobic crosslinking procedures of the invention are more effective than currently employed formalin treatments for inactivating viruses.

Thus, this indicates that not only are viral membrane proteins inactivated by the crosslinking and/or detergent treatment steps, but that viral replication functions are substantially inactivated. Hence, the viral inactivation methods of the invention are highly effective because they involve several inactivation steps and inactivate several viral functions.

The inactivation procedures of the invention generate inactive viruses that may be also used in conjunction with Aldrithiol inactivation procedures to generate inactive HIV that comply with the requirements of the FDA. As provided by the present invention, mechanistically independent methods of inactivation are useful for providing a prophylactic (e.g., AIDS or HIV) vaccine. Thus, the present methods involve a combination of chemical crosslinking (inactivating protein), irradiation with UV light (inactivating protein and nucleic acids) and detergent (dissolving poorly crosslinked viruses) treatments, where each of these treatments are capable of inactivating essentially all viruses. Such a combination of inactivation procedures helps to insure that only inactive viruses are present in the immunological compositions and vaccines of the invention.

The invention provides a method that can universally inactivate viruses, bacteria, parasites and tumor cells in a way that they can be safely used as immunological compositions or vaccines to inhibit the disease they cause. The inactivation kills the organism or cell in a specific manner that maintains its structure and conformation. Hence, the structure of the inactivated virus/cell is similar to that of the live virus/cell. In this way, the immunogenicity of the organism or cell as a whole is maintained and can be safely used to stimulate the immune system of a subject animal or patient. Similarly, the inactivated viruses, bacteria, cancer cells or parasites of the invention can be used for vaccination without causing disease or other negative side effects.

A study conducted by the inventors showed that INA treatment of tumor cells blocked their ability to divide and form colonies, with no detectable damage to the structural integrity of the cells.

Figure 12:
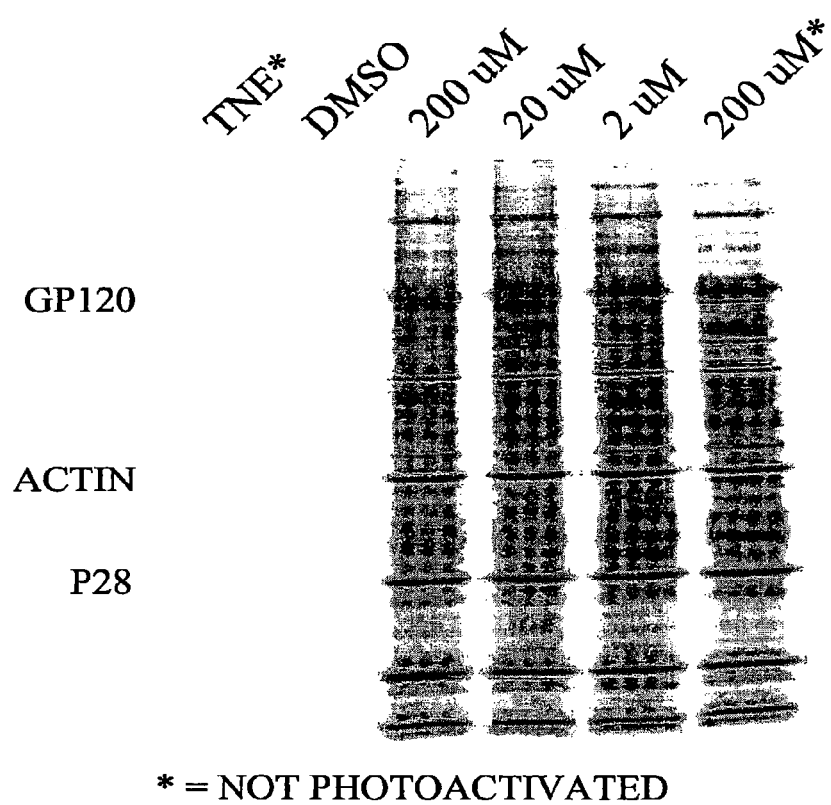
FIG. 12 illustrates that the integrity of SIV proteins was substantially unaffected by INA treatment. The integrity of the virus after the INA treatment was evaluated by recovery of the virus in the pellet using standard procedures for centrifugation of virus and by identifying the major viral proteins in the pellet by SDS-PAGE. Similar results were obtained with INA treated HIV (not shown).
Figure 13:
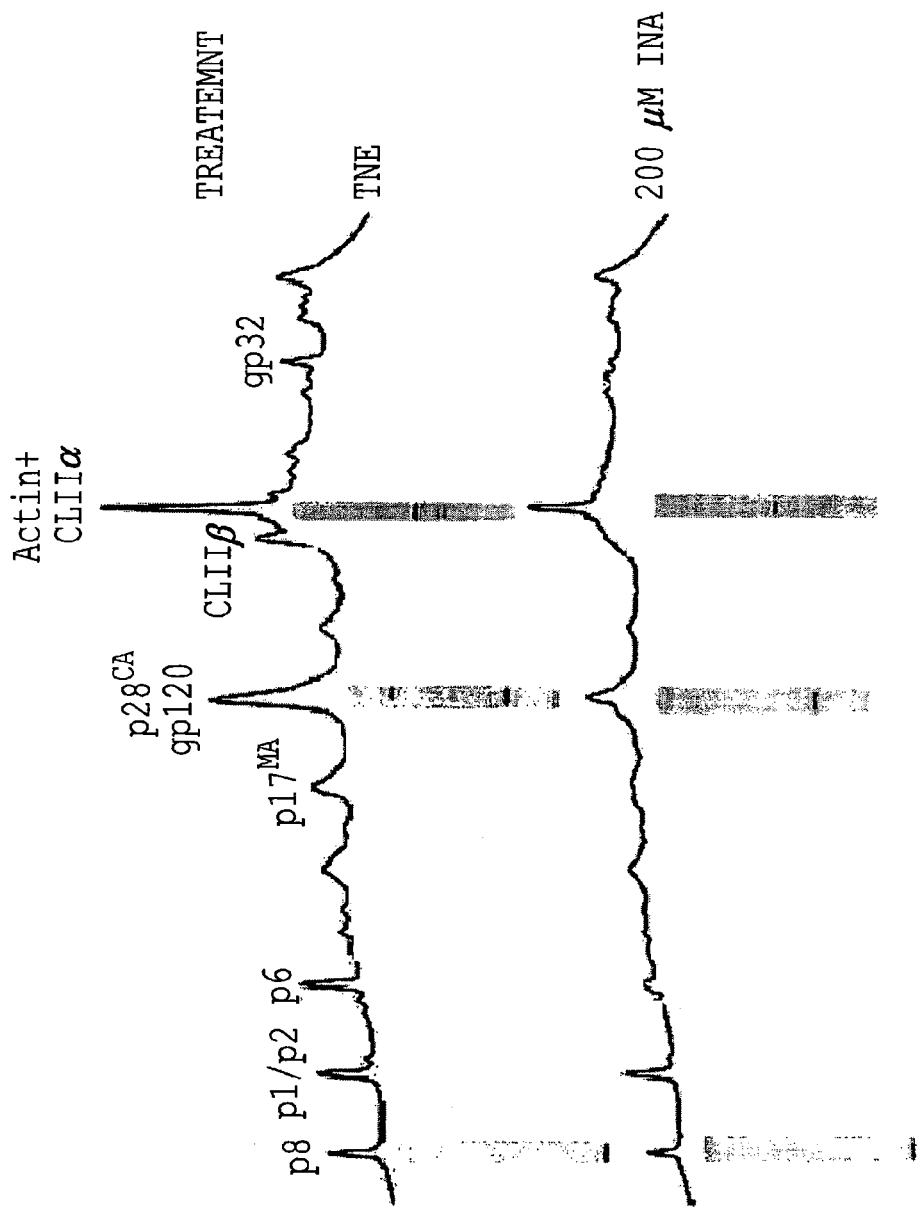
FIG. 13 shows that all detected viral proteins in INA-treated viruses were modified to some extent by INA as measured by their migration patterns on a reverse phase HPLC column. Hence, while the molecular masses of INA-treated viral proteins as observed by SDS-PAGE in FIG. 1 were not changed, some chemical modifications could be observed with HPLC.
Figure 14:
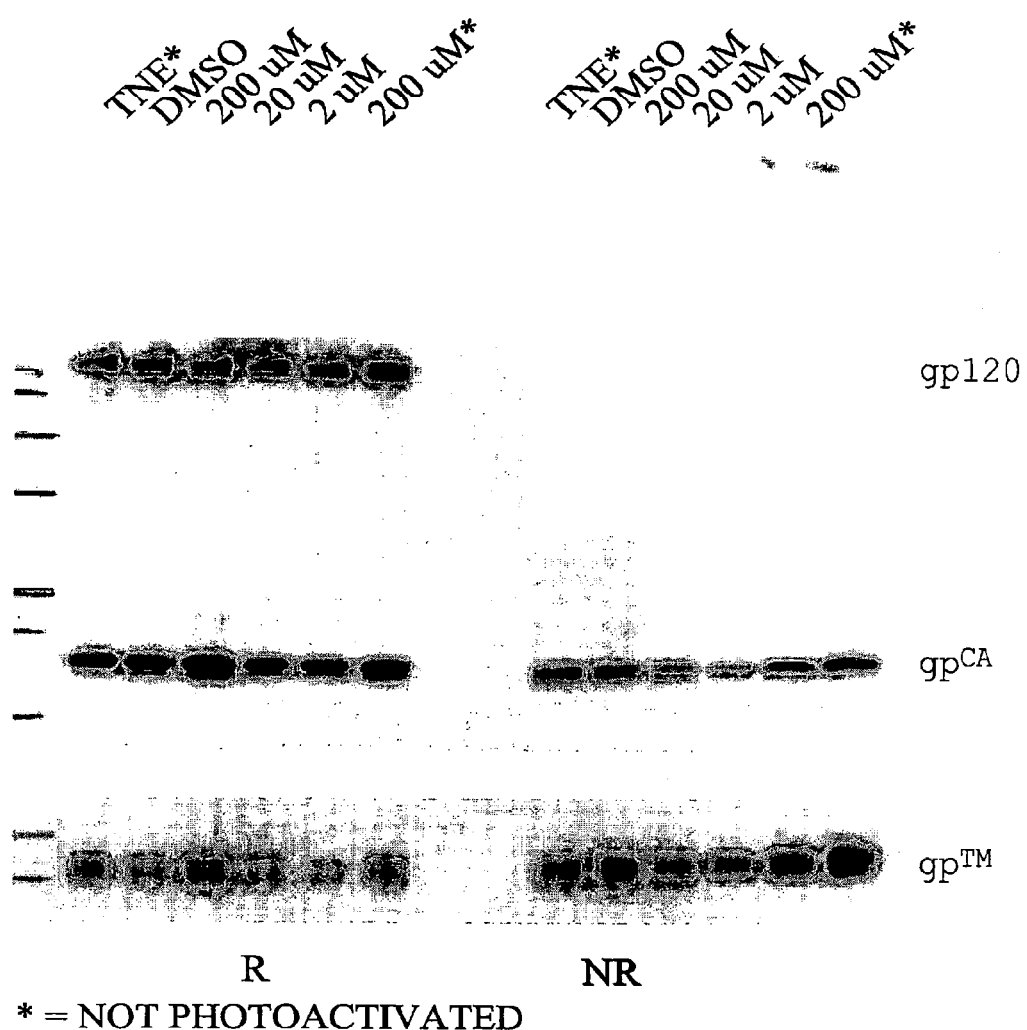
FIG. 14 shows that viral proteins from INA treated virus were still recognized by monoclonal antibodies as revealed by western blot analysis under reducing (R) and non-reducing (NR) conditions.
Figure 15:
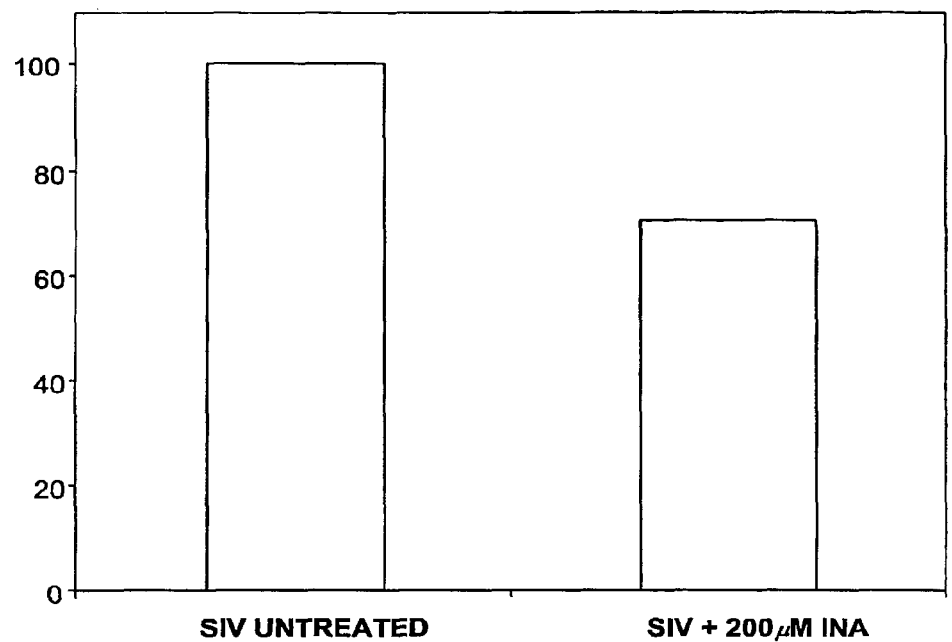
FIG. 15 shows that treatment of SW with 200 μM INA, which completely inactivated the SW (see Table 2), decreased CD4-independent binding of SIV to target cells by only 30%. Binding was measured by incubation of the virus with cells at room temperature. The cells were washed to remove unbound virus and the amount of gp32 that remained attached to the cells was measured by western blot analysis. CD4 dependent binding was not determined
Figure 16:
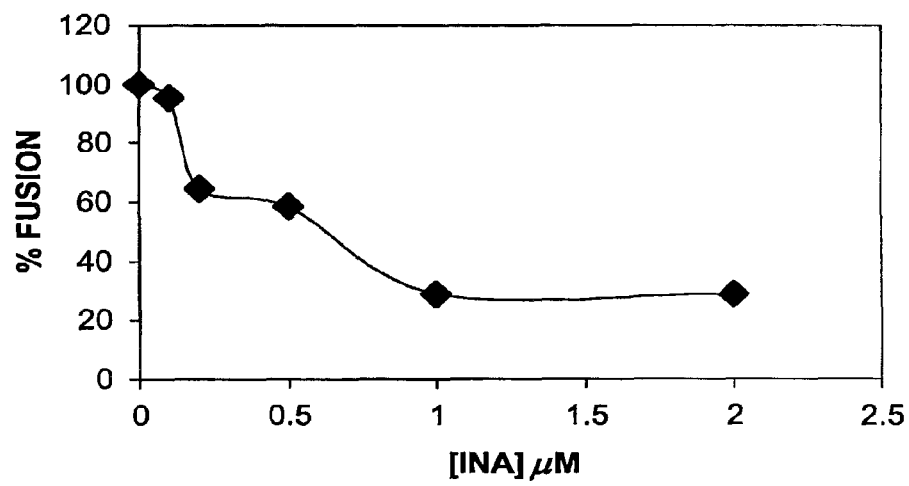
FIG. 16 illustrates that INA treatment blocks fusion of SIV with the target cell at the plasma membrane level, as measured by a photosensitized labeling method developed by the inventors. See Raviv et al. (2002) Virology, 293, 243-251.
Figure 17:
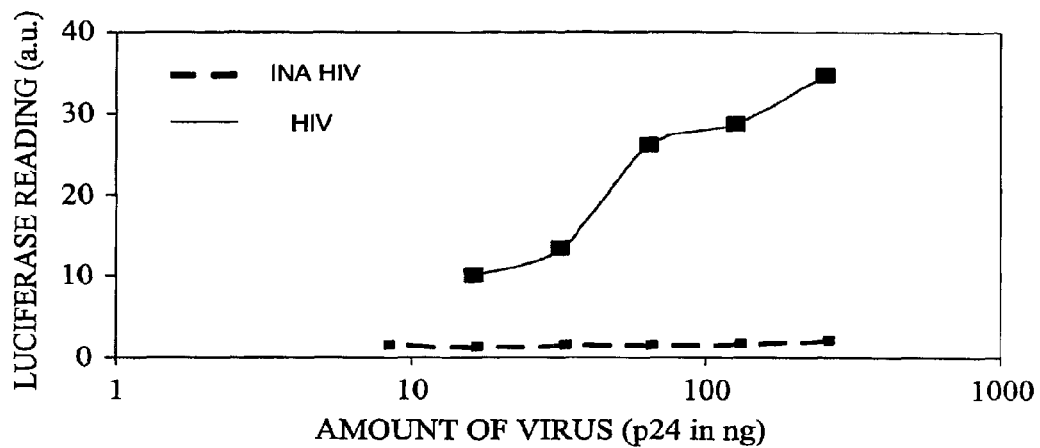
FIG. 17 illustrates the effect of INA treatment on HIV infectivity as measured by a luciferase reporter gene assay. As illustrated, INA-treated HIV exhibit essentially no transcription from viral promoters within the HIV LTR. These results further confirm that the INA-treated viruses used to generate the results in FIG. 1 were indeed inactivated.
Figure 18:
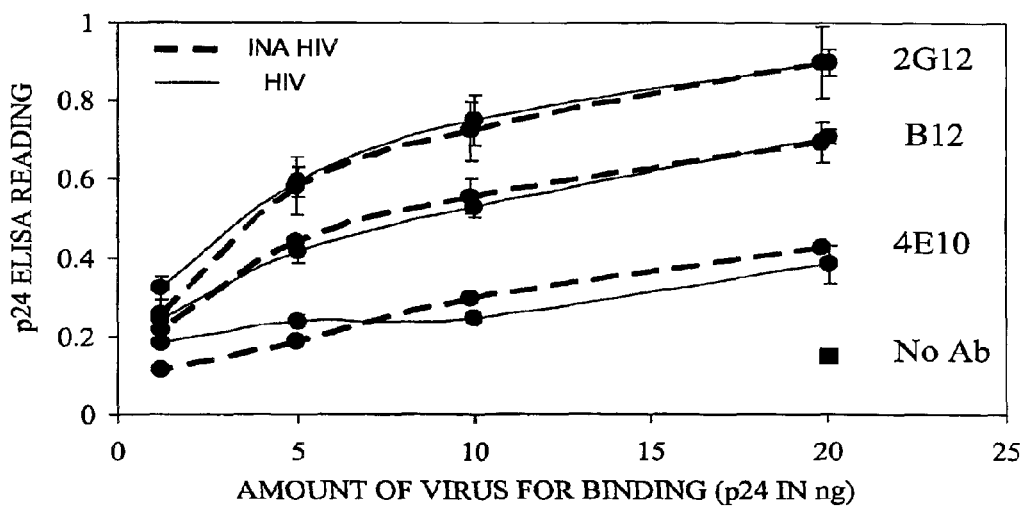
FIG. 18 illustrates that INA-treatment of HIV causes substantially no change in the epitopes recognized by three anti-HIV neutralizing antibody preparations. The antibody preparations tested were the 2G12, B12 and 4E10 antibody preparations. As shown, the amount of virus bound by the three antibody preparations did not change when HIV was treated with INA (dashed lines) as compared to untreated HIV (solid lines).

Studies by the inventors show that INA can also be used to inactivate live HIV, SIV and Ebola viruses. In particular, INA treatment produced inactive viruses with no detectable infectivity (Table 2 and FIG. 17) and with no significant change to their structural integrity (FIGS. 12, 14 and 15). Minor modifications to viral proteins were detected (FIG. 13). However, these modifications did not affect the ability of these proteins to react with antibodies that are known to bind to SIV or HIV (FIGS. 14 and 18). Likewise, the inactive virus was not significantly impaired in its ability to bind to target cells, with the highest concentration of INA (0.2 mM) only reducing the binding by 30% (FIG. 15). However, the INA treatment impaired the ability of the virus to fuse with the target cell at the plasma membrane level (FIG. 16) and to express virally encoded functions (FIG. 17). Viral growth in cells that normally would become infected was essentially eliminated.

Hence, the INA treatment procedures of the invention generate inactive viruses that can be used in a manner similar to aldrithiol inactivated HIV (developed by the AIDS vaccine program SAIC). Alternatively, the INA-inactivation procedures of the invention can be used in conjunction with aldrithiol inactivation procedures to generate inactive HIV that comply with the requirements of the FDA. Thus, two mechanistically independent methods of inactivation can be used to provide a prophylactic AIDS or HIV vaccine.

The present invention is therefore directed to methods of treating or preventing or otherwise ameliorating viral infections in animals, including humans as well as animals such as farm animals, domestic animals, zoo animals and birds. These methods include administering to the mammal or animal an effective amount, for example, a therapeutically effective amount, of an inactivated virus of the present invention. Viruses selected for inactivation by the present methods are those that can cause an infection in an animal, for example, in any of the mammals or birds described herein.

Prevention, inhibition or treatment of viral infections is intended to include the alleviation of or diminishment of at least one symptom typically associated with the infection. Prevention, inhibition or treatment also includes alleviation or diminishment of more than one symptom. Ideally, treatment with the inactivated viruses of the invention generates an immune response in the animal towards the virus while prevention by the inactivated viruses of the invention gives rise to immunity in the animal that substantially eliminates the symptoms associated with the infection.

Exemplary viral infections that may be treated by the present inactivated agents include infections by any virus that may infect animals (including but not limited to mammals and birds), including enveloped and non-enveloped viruses, DNA and RNA viruses, viroids, and prions. In some embodiments, the virus is an enveloped virus. For example, infections or unwanted levels of the following viruses and viral types may be treated, prevented or addressed by the present inactivated agents: human immunodeficiency virus (HIV), simian immunodeficiency virus (SIV), influenza, hemorrhagic fever viruses, hepatitis A virus, hepatitis B virus, hepatitis C virus, poxviruses, herpes viruses, adenoviruses, papovaviruses, parvoviruses, reoviruses, orbiviruses, picornaviruses, rotaviruses, alphaviruses, rubiviruses, influenza viruses (type A and B), flaviviruses, coronaviruses, paramyxoviruses, morbilliviruses, pneumoviruses, rhabdoviruses, lyssaviruses, orthomyxoviruses, bunyaviruses, phleboviruses, nairoviruses, hepadnaviruses, arenaviruses, retroviruses, enteroviruses, rhinoviruses and the filovirus.

Infections or unwanted levels of the following target viruses and viral types that are believed to have potential as biological weapons may be treated, prevented or addressed by the present inactivated agents: hemorrhagic fever viruses (HFVs), Chikungunya virus, Japanese encephalitis virus, Monkey pox virus, variola virus, Congo-Crimean hemorrhagic fever virus, Junin virus, Omsk hemorrhagic fever virus, Venezuelan equine encephalitis virus, Dengue fever virus, Lassa fever virus, Rift valley fever virus, Western equine encephalitis virus, Eastern equine encephalitis virus, Lymphocytic choriomeningitis virus, Russian Spring-Summer encephalitis virus, White pox, Ebola virus, Machupo virus, Smallpox virus, Yellow fever virus, Hantaan virus, Marburg virus, and Tick-borne encephalitis virus.

Anti-viral activity can be evaluated against these varieties of viruses using methods available to one of skill in the art. In one embodiment, anti-viral activity is the amount of the inactivated virus that stimulates an immune response against the virus. In another embodiment, anti-virus activity is the amount of the inactivated virus that effectively immunizes a mammal or bird against the virus. In a further embodiment, anti-viral activity is the amount that reduces the viral load detected in the animal. For example, the viral load can be reduced to less than 50,000 viral copies per ml of plasma, or less than 10,000 viral copies per ml of plasma, or less than 5,00 viral copies per ml.

Similarly, infections or unwanted levels of the following examples of target microbial organisms can be treated, prevented or addressed by the present inactivated agents: *Aeromonas* spp. (including, for example, *Aeromonas hydrophila, Aeromonas caviae* and *Aeromonas sobria*), *Bacillus* spp. (including, for example, *Bacillus cereus, Bacillus anthracis* and *Bacillus thuringiensis*), *Bacteroides* spp. (including, for example, *B. fragilis, B. thetaiotaomicron, B. vulgatus, B. ovatus, B. distasonis, B. uniformis, B. stercoris, B. eggerthii, B. merdae,* and *B. caccae*), *Campylobacter* spp. (including, for example, *Campylobacter jejuni, Campylobacter laridis,* and *Campylobacter hyointestinalis*), *Clostridium* spp. (such as the pathogenic clostridia including all types of *Clostridium botulinum* (including those in Groups I, II, III and IV, and including those that produce botulism A, B, C, D, E, F and G), all types of *Clostridium tetani*, all types of *Clostridium difficile*, and all types of *Clostridium perfringens*), *Ebola* spp. (e.g. EBOV Zaire), *Enterobacter* spp. (including, for example, *Enterobacter aerogenes* (also sometimes referred to as *Klebsiella mobilis*), *Enterobacter agglomerans* (also sometimes referred to as *Pantoea agglomerans*), *Enterobacter amnigenus, Enterobacter asburiae, Enterobacter cancerogenus* (also sometimes referred to as *Enterobacter taylorae* and/or *Erwinia cancerogena*), *Enterobacter cloacae, Enterobacter cowanii, Enterobacter dissolvens* (also sometimes referred to as *Erwinia dissolvens*), *Enterobacter gergoviae, Enterobacter hormaechei, Enterobacter intermedium, Enterobacter intermedius* (also sometimes referred to as *Enterobacter intermedium*), *Enterobacter kobei, Enterobacter nimipressuralis* (also sometimes referred to as *Erwinia nimipressuralis*), *Enterobacter sakazakii*, and *Enterobacter taylorae* (also sometimes referred to as *Enterobacter cancerogenus*)), *Enterococcus* spp. (including, for example, Vancomycin Resistant *Enterococcus* (VRE), *Enterococcus faecalis, Enterococcus faecium, Enterococcus durans, Enterococcus gallinarum*, and *Enterococcus casseliflavus*), *Escherichia* spp. (including the enterotoxigenic (ETEC) strains, the enteropathogenic (EPEC) strains, the enterohemorrhagic (EHEC) strain designated *E. coli* O157:H7, and the enteroinvasive (EIEC) strains), *Gastrospirillum* spp. (including, for example, *Gastrospirillum hominis* (also sometimes now referred to as *Helicobacter heilmannii*), *Helicobacter* spp. (including, for example, *Helicobacter pylori* and *Helicobacter hepaticus*), *Klebsiella* spp. (including, for example, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*), *Salmonella* spp. (including, for example, *S. typhi* and *S. paratyphi* A, B, and C, *S. enteritidis*, and *S. dublin*), *Shigella* spp. (including, for example, *Shigella sonnei, Shigella boydii, Shigella flexneri,* and *Shigella dysenteriae*), *Staphylococcus* spp. (including, for example, *Staphylococcus aureus*, methicillin-resistant *Staphylococcus aureus* (MRSA), *Staphylococcus saprophyticus* and *Staphylococcus epidermis*), *Streptococcus* ssp. (including Groups A (one species with 40 antigenic types, *Streptococcus pyogenes*), B, C, D (five species (*Streptococcus faecalis, Streptococcus faecium, Streptococcus durans, Streptococcus avium,* and *Streptococcus bovis*)), F, and G, including *Streptococcus pneumoniae*), *Pseudomonas* spp. (including, for example, *Pseudomonas aeruginosa, Pseudomonas maltophilia, Pseudomonas fluorescens, Pseudomonas putida, Pseudomonas cepacia, Pseudomonas stutzeri, Pseudomonas mallei, Pseudomonas pseudomallei* and *Pseudomonas putrefaciens*), *Vibrio* spp. (including, for example, *Vibrio cholera* Serogroup O1 and *Vibrio cholera* Serogroup Non-O1, *Vibrio parahaemolyticus, Vibrio alginolyticus, Vibrio furnissii, Vibrio carchariae, Vibrio hollisae, Vibrio cincinnatiensis, Vibrio metschnikovii, Vibrio damsela, Vibrio mimicus, Vibrio vulnificus,* and *Vibrio fluvialis*), *Yersinia* spp. (including, for example, *Yersinia pestis, Yersinia enterocolitica* and *Yersinia pseudotuberculosis*), *Neisseria, Proteus, Citrobacter, Aerobacter, Providencia, Serratia, Brucella, Francisella tularensis* (also sometimes referred to as *Pasteurella tularensis, Bacillus tularensis, Brucella tularensis,* tularemia, rabbit fever, deerfly fever, Ohara's disease, and/or Francis disease), and the like. Thus, for example, various bacterial infections or unwanted levels of bacteria that can be treated, prevented or addressed by the present inactivated agents include but are not limited to those associated with anthrax (*Bacillus anthracis*), staph infections (*Staphylococcus aureus*), typhus (*Salmonella typhi*), food poisoning (*Escherichia coli*, such as O157:H7), bascillary dysentery (*Shigella dysenteria*), pneumonia (*Psuedomonas aerugenosa* and/or *Pseudomonas cepacia*), cholera (*Vibrio cholerae*), ulcers (*Helicobacter pylori*), *Bacillus cereus*, *Salmonella*, *Clostridium perfringens*, *Campylobacter*, *Listeria monocytogenes*, *Vibrio parahaemolyticus*, botulism (*Clostridium botulinum*), smallpox (variola major), listeriosis (*Listeria monocytogenes*), tularemia (*Francisella tularensis*), plague (*Yersinia pestis*; also sometimes referred to as bubonic plague, pneumonic plague, and/or black death) and others. *E. coli* serotype O157:H7 has been implicated in the pathogenesis of diarrhea, hemorrhagic colitis, hemolytic uremic syndrome (HUS) and thrombotic thrombocytopenic purpura (TTP). As indicated herein, the inactivated agents of the invention are also active against drug-resistant and multiply-drug resistant strains of bacteria, for example, multiply-resistant strains of *Staphylococcus aureus* and vancomycin-resistant strains of *Enterococcus faecium* and *Enterococcus faecalis*.

Fungal infections that can be treated or prevented by the present inactivated agents include infections by fungi that infect a mammal, including *Histoplasma capsulatum*, *Coccidioides immitis*, *Cryptococcus neoformans*, *Candida* ssp. including *Candida albicans*, *Aspergilli* ssp. including *Aspergillus fumigatus*, *Sporothrix*, *Trichophyton* ssp., *Fusarium* ssp., *Tricosporon* ssp., *Pneumocystis carinii*, and *Trichophyton mentagrophytes*. Hence, for example, infections or unwanted levels of target fungi can be treated, prevented or addressed by the present inactivated agents. Such fungi also include fungal pathogens that may have potential for use biological weapons, including *Coccidioides immitis* and *Histoplasma capsulatum*. Anti-microbial activity can be evaluated against these varieties of microbes (viruses, bacteria, fungi and parasites) using methods available to one of skill in the art. In one embodiment, anti-microbial activity is the amount of the inactivated agent that stimulates an immune response against the microbe. In another embodiment, anti-microbial activity is the amount of the inactivated agent that effectively immunizes a mammal against the microbe. Treatment of, or treating, cancer is intended to include the alleviation of or diminishment of at least one symptom typically associated with the disease. The treatment also includes alleviation or diminishment of more than one symptom. The treatment may cure the cancer, e.g., it may reduce the number of cancer cells and/or arrest the growth of the cancerous tumor.

Cancers that can be treated by the present inactivated agents include solid mammalian tumors as well as hematological malignancies. Solid mammalian tumors include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Information regarding numerous types of cancer can be found, e.g., from the American Cancer Society (www.cancer.org), or from, e.g., Wilson et al. (1991) Harrison's Principles of Internal Medicine, 12.sup.th Edition, McGraw-Hill, Inc. Both human and veterinary uses are contemplated.

Anti-cancer activity can be evaluated against varieties of cancers using methods available to one of skill in the art. Anti-cancer activity, for example, is determined by identifying the $LD_{100}$ or $ED_{50}$ of an inactivated tumor or cancer cell of the present invention that prevents the growth of a cancer. In one embodiment, anti-cancer activity is the amount of the inactivated agent that effectively immunizes a mammal against that cancer type.

According to the present invention, the inactivated agents provided herein do not have substantial or undesired toxicity or infectivity within the mammalian organism to be treated According to the present invention, the inactivated viruses provided herein do not have substantial or undesired toxicity or infectivity within the organism to be treated.

The present methods for inactivating viruses can be used not only for making therapeutic compositions containing inactivated viruses the invention may also be applied to basic research, where non-infectious virus particles may be used as a safer alternative to their infectious counterparts. Because the inactivated viral particles are non-infectious, and are substantially whole virions or retain native viral structures, they could be used in immunological studies, nanotechnology, assay development, where BL3 level containment may not be available.

Administration of the Inactivated Agents

The inactivated agent preparations and crosslinked particles ("therapeutic agents") of the invention are administered so as to achieve a reduction in at least one symptom associated with a disease such as a infection, cancer, tumor, or other disease, or a decrease in viral load detectable in a subject suffering from a viral infection, or inhibition of viral infection in a subject who may have been or who may later be exposed to a viral infection. The inactivated agents of the invention are also administered so as to achieve a decrease in the amount of antibody associated with the infection, cancer tumor, or other disease.

To achieve the desired effect(s), the inactivated agent, or a combination of inactivated agents, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the inactivated agent chosen, the disease, the weight, the physical condition, the health, the age of the animal, or whether prevention or treatment is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of certain therapeutic agents and inactivated viral preparations of the invention can be intermittent over a preselected period of time, for example, in a series of spaced doses. Both local and systemic administration is contemplated.

To prepare the composition, inactivated agents and crosslinked particles are prepared according to the methods described herein, and purified as necessary or desired. In some embodiments, the inactivated agents and crosslinked particles can be lyophilized and/or stabilized. The selected therapeutic agent(s) can then be adjusted to the appropriate concentration, and optionally combined with other agents.

The absolute weight of a given inactivated agent preparation included in a unit dose may vary widely. For example, about 0.01 to about 2 g, or about 0.1 to about 500 mg, of at least one inactivated agent preparation of the invention, or a plurality of inactivated agent strains, types or species, can be administered. Alternatively, the unit dosage may vary from about 0.01 g to about 5 g, from about 0.01 g to about 3.5 g, from about 0.01 g to about 2.5 g, from about 0.1 g to about 1 g, from about 0.1 g to about 0.8 g, from about 0.1 g to about 0.4 g, or from about 0.1 g to about 0.2 g.

One or more suitable unit dosage forms comprising the therapeutic agents of the invention may be administered by a variety of routes including by oral, parenteral (including subcutaneous, intravenous, intramuscular and intraperitoneal), rectal, dermal, transdermal, intrathoracic, intrapulmonary and intranasal (respiratory) routes. The therapeutic inactivated viruses may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the inactivated viruses with liquid carriers, solid matrices, semi-solid carriers, finely divided solid carriers or combinations thereof, and then, if necessary, introducing or shaping the product into the desired delivery system.

When the therapeutic agents are prepared for oral administration, they are generally combined with a pharmaceutically acceptable carrier, diluent or excipient to form a pharmaceutical formulation, or unit dosage form. For oral administration, the inactivated agents may be present as a powder, a granular formulation, a solution, a suspension, an emulsion or in a natural or synthetic polymer or resin for ingestion of the agents from a chewing gum. The therapeutic agents including the inactivated agents may also be presented as a bolus, electuary or paste. Orally administered the therapeutic agents of the invention may also be formulated for sustained release, e.g., the inactivated viruses may be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic agents may be prepared by procedures described herein and formulated using procedures known in the art using wellknown and readily available ingredients. For example, the inactivated viruses and cross-linked virus-like particles may be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents may also be included such as carboxymethyl cellulose, hydroxymethylcellulose, hydroxypropyl methylcellulose and other cellulose derivatives, alginates, gelatin, and polyvinyl-pyrrolidone. Moisturizing agents may be included such as glycerol, disintegrating agents such as calcium carbonate and sodium bicarbonate. Agents for retarding dissolution may also be included such as paraffin. Resorption accelerators such as quaternary ammonium compounds may also be included. Surface active agents such as cetyl alcohol and glycerol monostearate may be included. Adsorptive carriers such as kaolin and bentonite may be added. Lubricants such as talc, calcium and magnesium stearate, and solid polyethyl glycols may also be included. Preservatives may also be added. The compositions of the invention may also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention may include buffering agents such as calcium carbonate, magnesium oxide and magnesium carbonate. Caplets and tablets may also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one inactivated agent of the invention may contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more inactivated agents of the invention are designed to resist disintegration in the stomach and dissolve in the more neutral to alkaline environment of the duodenum.

The therapeutic agents of the invention may also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention may also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives may be added to help maintain the shelf life of the dosage form. The inactivated agents, crosslinked virus-like particles and/or other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

These formulations may contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes. In some embodiments, the therapeutic agents are formulated in aqueous solutions, for example, in saline or buffered saline solutions.

It is possible to add, if desired, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives may be added.

Also contemplated are combination products that include one or more therapeutic agents of the present invention and one or more anti-microbial agents. For example, a variety of antibiotics may be included in the pharmaceutical compositions of the invention, such as aminoglycosides (e.g., streptomycin, gentamicin, sisomicin, tobramycin and amicacin), ansamycins (e.g. rifamycin), antimycotics (e.g. polyenes and benzofuran derivatives), β-lactams (e.g. penicillins and cephalosporins), chloramphenical (including thiamphenol and azidamphenicol), linosamides (lincomycin, clindamycin), macrolides (erythromycin, oleandomycin, spiramycin), polymyxins, bacitracins, tyrothycin, capreomycin, vancomycin, tetracyclines (including oxytetracycline, minocycline, doxycycline), phosphomycin and fusidic acid.

Additionally, the therapeutic agents are well suited to formulation as sustained release dosage forms and the like. The formulations may be so constituted that they release a cross-linked virus-like particle or an inactivated agent, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the crosslinked virus-like particles and/or inactivated agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention may be delivered via patches or bandages for dermal administration. Alternatively, the therapeutic agents may be formulated to be part of an adhesive polymer, such as polyacrylate or acrylate/vinyl acetate copolymer. For long-term applications it might be desirable to use microporous and/or breathable backing laminates, so hydration or maceration of the skin may be minimized. The backing layer may be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The therapeutic agents may also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops may be delivered via a simple eye dropper-capped bottle, or via a plastic bottle adapted to deliver liquid contents dropwise, via a specially shaped closure.

The therapeutic agents may further be formulated for topical administration in the mouth or throat. For example, the active ingredients may be formulated as a lozenge further comprising a flavored base, for example, sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The therapeutic agents of the invention may also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific viral infection or disease. Any statistically significant attenuation of one or more symptoms of an infection or disease that has been treated pursuant to the methods of the present invention is considered to be a treatment or prevention of such infection or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in AEROSOLS AND THE LUNG, Clarke, S. W. and Davia, D. eds., pp. 197-224, Butterworths, London, England, 1984).

Therapeutic agents of the present invention may also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated or prevented. Dry aerosol in the form of finely divided solid inactivated agent that are not dissolved or suspended in a liquid are also useful in the practice of the present invention. Therapeutic agents of the present invention may be formulated as dusting powders and comprise finely divided particles having an average particle size of between about 1 and 5 μM, alternatively between 2 and 3 μM. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating or preventing the particular infection, indication or disease since the necessary effective amount may be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the inactivated agent preparations and cross-linked virus-like particles may also be used in combination with other therapeutic agents, for example, pain relievers, anti-inflammatory agents, antihistamines, bronchodilators and the like, whether for the conditions described or some other condition.

The present invention further pertains to a packaged pharmaceutical composition for controlling infections or cancer such as a kit or other container. The kit or container holds a therapeutically effective amount of a pharmaceutical composition for controlling microbial infections or cancer or tumor growth and instructions for using the pharmaceutical composition for control of the infection or for control of the cancer or tumor. The pharmaceutical composition includes at least one inactivated agent preparation of the present invention, in a therapeutically effective amount such that an infection, cancer, or tumor is controlled.

The invention is further illustrated by the following non-limiting Examples.

EXAMPLES

Example 1

Crosslinking Viral Membrane Proteins with 1,5-Diazidonaphthalene

This Example shows that 1,5-diazidonaphthalene (DAN) crosslinks transmembrane and capsid proteins in HIV-1 and that viral structures are not compromised after such crosslinking.
Methods
Viruses HIV-1 (MN)/H9 clone 4 (lot #P3592 and lot #P3602; provided by the AIDS Vaccine Program) was propagated in H9 cells, as described previously (Ott at al. 1995). Concentrated virus preparations were produced by sucrose gradient banding in a continuous-flow centrifuge (Bess at al. 1997).
Treatment with Hydrophobic Crosslinkers HIV-1$_{MN}$ viruses were suspended in Phosphate Buffered saline (PBS) at a concentration of 0.5-1.0 mg/ml. A stock solution of 8.0-8.69 mM crosslinkers (e.g., DAN) in DMSO was prepared. The crosslinker solution was added to the viral suspension under dim light to a final concentration of 100 µM. The suspension was then irradiated at a wavelength of 300 nm (or higher) using an ozone free 100 W mercury arc lamp through a water filter to eliminate heat. The time of irradiation may be varied with the size of the sample but was typically from 2 to 15 minutes.

To observe the effects of crosslinkers such as 1,5-diazidonaphthalene (DAN) on HIV-1 transmembrane and capsid proteins, samples of control and crosslinked virion proteins were subjected to SDS-PAGE electrophoresis and western blotting to permit separation and assessment of viral protein molecular weights and reactivity with selected antibodies. In addition, whole, cross-linked HIV virions were visualized by transmission electron microscopy (TEM).
Viral Infectivity An infectivity assay was carried out using the luciferase reporter gene assay, essentially as described by Spenlehauer et al. (2001) Virology 280, 292-300; and Wei et al. (2002) Antimicrobial Agents and Chemotherapy, 46, 1896-1905. Briefly, TZM-bl cells were used that express the luciferase enzyme under the transcriptional control of HIV long terminal repeat (LTR). Upon HIV infection, the TAT protein from the virus binds to the LTR to induce the expression of Luciferase. The level of Luciferase expression can be assessed by incubation of the sample with a luciferase substrate, which triggers a chemiluminescent signal that can be easily quantified by a luminometer.

In a separate assay, DNA was extracted from HIV-1 MN infected supT1 cells 21 days post-infection and viral infection was measured by amplification of HIV gag sequences using polymerase chain reaction (PCR).

Results

FIG. 1 shows a western blot of electrophoretically separated virion proteins stained with anti-gp41, anti-p24, anti-HLADR, anti-p17 or anti-gp120 antibodies. When virions were subjected to crosslinking by 1,5-diazidonaphthalene (DAN), virion proteins generally had a higher molecular weight than uncrosslinked control proteins. Thus, some of the gp41, p24, p17 and gp120 proteins were detected as high molecular weight (crosslinked) proteins rather than at the lower molecular weight where they are normally detected.

Moreover, TEM images of HIV-1 MN viral particles before and after crosslinking indicate that crosslinking with 1,5-diazidonaphthalene did not adversely affect the structure of these viruses. In particular, virion (V) structures including microvesicles (Vsc) are visible after treatment of HIV-1 MN virions with 1,5-diazidonaphthalene followed by UV irradiation for 15 minutes (FIG. 2).

The combination of UV irradiation and the crosslinker was a dual inactivation step. In addition to a decrease in infectivity from UV irradiation, the use of the hydrophobic crosslinker that targets both the transmembrane and capsid proteins also caused the virus to completely lose its infectivity as measured by luminescence and PCR assays. In particular, as shown in FIG. 3, substantially no luciferase expression is detected after TZM-bl cells were exposed to DAN-treated HIV. However, HIV viruses that were not exposed to DAN+UV readily induced expression of luciferase. Similarly, assays for detecting HIV nucleic acids 21 days after exposure of host cells to DAN-treated HIV by PCR amplification assay of viral gag sequences showed that cells exposed to DAN-treated HIV had essentially no HIV gag transcripts or gag genomic sequences (FIG. 4).

Example 2

Detergent-Inactivation of Viruses

This Example shows that 1,5-diazidonaphthalene (DAN) crosslinks transmembrane and capsid proteins in HIV-1 and that viral structures are not compromised after such crosslinking.

Methods

HIV-1 MN virions were treated with 100 µM of 1,5-diazidonaphthalene (DAN) and then irradiated with UV light for 15 minutes to crosslink viral membrane proteins as described in Example 1. After crosslinking, the virions were treated with 1% Triton X100 at 37° C. for 1 hour. As a control, HIV virions were subjected to the same detergent treatment but with no DAN crosslinking. Both control and test viral particles were separated from the detergent and other impurities by centrifugation in an Optima TLX Ultracentrifuge (TLA 120.1 rotor) using a 23% sucrose cushion at 45,000 rpm for 35 minutes. The pellet containing viral particles was isolated. Recovery of viral particles was evaluated by measuring the amount of the transmembrane protein gp41 present in the pellet using SDS-PAGE to separate viral proteins, western blotting and use of anti-gp41 antibodies to detect viral gp41 proteins.

Results

As shown in FIG. 5, high molecular weight proteins were observed in pelleted viral samples that had been subjected to DAN crosslinking followed by detergent treatment. However, no such high molecular weight proteins were observed when viral particles were subjected to detergent treatment without DAN crosslinking. Moreover, when the crosslinked virus is subsequently treated with detergent, viral antigens were recovered by sedimentation through a sucrose cushion, whereas fewer viral antigens were detected after sedimentation of the uncrosslinked detergent-treated control (FIG. 5). These data indicate that crosslinking of viral membrane proteins helps preserve viral structures and may maintain the integrity of at least some portions of the viral particle during detergent treatment. Without crosslinking, viral particles are essentially dissolved and dissociated by detergent treatment.

Example 3

INA (1-azido-5-iodonaphthalene) as a Crosslinker

This Example illustrates that INA (1-azido-5-iodonaphthalene) is an effective crosslinking agent for viral inactivation when INA is used with ultraviolet irradiation.

Methods

To test the effectiveness of INA, 100 uM of either DAN, or INA, or DMSO (control) was combined with HIV virions (0.5 mg/mL) and the mixture was exposed to UV irradiation (while no UV filter was used, the wavelength greater than 280 or greater than 330 nm) for 15 minutes. The structures of DAN and INA are shown below.

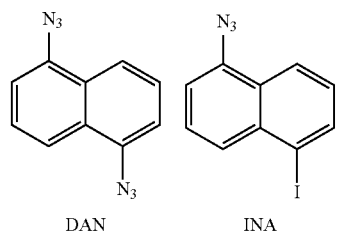

A portion of the mixture was then electrophoretically separated and a western blot was prepared. The blot was stained for the transmembrane protein in HIV (41).

Results

Figure 6:
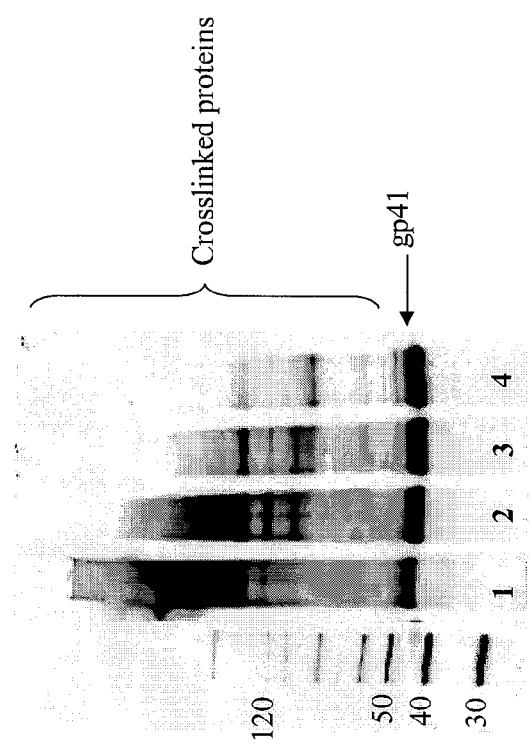
FIG. 6 illustrates that INA (1-azido-5-iodonaphthalene) is an effective crosslinking agent for viral inactivation when a mixture of viral particles and INA is exposed to ultraviolet irradiation. A western blot of electrophoretically separated HIV proteins is shown after the HIV virions were treated with INA, DAN (positive control) or DMSO (negative control). The blot has been stained for the transmembrane protein in HIV (gp41). Lane 1=HIV with INA+UV for 15 minutes, Lane 2=HIV with DAN+UV for 15 minutes, Lane 3=DMSO only+ UV for 15 minutes, Lane 4=HIV control (no UV, no DMSO). As illustrated by the appearance of higher molecular weight bands in the western blot INA can form crosslinks after UV irradiation for 15 minutes.

As shown in FIG. 6 bands are present in the INA treated HIV sample (lane 1) that have higher molecular weights than those observed for uncrosslinked HIV (lane 4). These data demonstrate that INA is an excellent crosslinking agent for viral proteins when used on live viruses with ultraviolet irradiation.

Example 4

Diverse Crosslinking Agents Effectively Inactivate Viruses

This Example illustrates that a variety of hydrophobic crosslinking compounds can effectively be used to crosslink and inactivate viruses, including the HIV-1 virus.

Compounds

Some of the crosslinking agents used in the experiments described herein have the following structures.

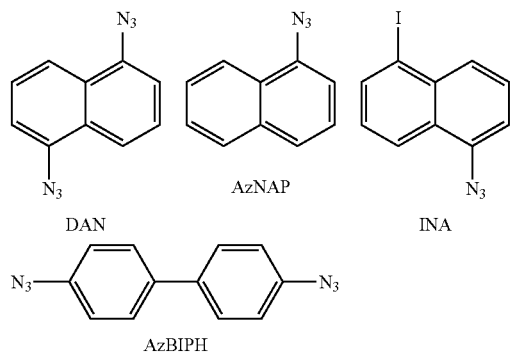

Certain control compounds were also employed including NAP, INAP, DIN and formaldehyde, having the following structures.

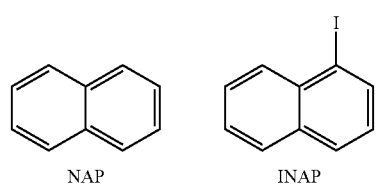

-continued

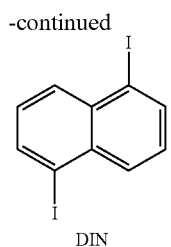

Formaldehyde        DIN

The synthetic procedures employed for making 1,5-diazidonaphthalene (DAN), 1-azidonaphthalene (AzNAP), and 4,4'-diazidobiphenyl (AzBIPH) were adapted from those of Smith and Brown 1951 and Ling 1992, using the commercially-available amino precursors of the compounds. Smith & Brown (1951) J. Am. Chem. Soc. 73 (6), 2438-2441; Ling et al. (1992) J. Am. Chem. Soc., 114(25), 9959-9969.

The synthetic procedures employed for making 1,5-diiodonaphthalene (DIN) were adapted from Rodriguez 2002, using the commercially-available diamino precursor. Rodriguez et al. (2002) J. Org. Chem., 67(22), 7631-7640.

Other compounds used were obtained from commercial sources.

Methods

Crosslinking conditions: The various crosslinkers and controls were prepared using 8 mM stock solutions in DMSO. Each stock was added to 0.5 mg HIV-1 MN total protein per ml, to yield a final concentration of 100 micromolar of the hydrophobic crosslinking compound. The mixture was then irradiated with UV for 2 or 15 minutes (as indicated in the figures) to crosslink the viral proteins. In some cases, a filter was placed between the ultraviolet light source and the viral solution to filter out light of wavelength 360 nm. This served as a control to test whether crosslinking was diminished when 360 nm light was blocked. Additional controls employed were 0.5 mg/mL HIV-1 MN with DMSO and UV treatment as well as HIV-1 MN without any DMSO or UV treatment. The various compounds tested were 1-azido-5-iodonaphthalene (INA), 1,5-diazidonaphthalene (DAN), 1-azidonaphthalene (AzNAP), 1-iodonaphthalene (INAP), and 1,5-diiodonaphthalene (DIN).

Western Analysis: After crosslinking, the proteins in the viral preparations were electrophoretically separated by SDS-polyacrylamide gel electrophoresis (SDS-PAGE). The SDS-PAGE was run under reducing conditions, followed by blotting onto nitrocellulose and immunological probing using anti-gp41, with AlexaFluor-conjugated secondary antibodies for infrared (1R) readout using the Odyssey IR imaging system.

Comparison to Formalin Crosslinking: The various crosslinkers and controls were prepared using 8 mM stock solutions in DMSO. Each stock was added to 0.5 mg HIV-1 MN total protein per ml, to yield a final concentration of 100 micromolar of hydrophobic compound. The mixture was then irradiated with UV for 15 minutes (as indicated in the description of FIG. 8) to crosslink the viral proteins. Controls employed were 0.5 mg/mL HIV-1 MN with DMSO and UV treatment and HIV-1 MN without any DMSO or UV treatment. The various crosslinking compounds tested were 1-azido-5-iodonaphthalene (INA) 1,5-diazidonaphthalene (DAN), 1-azidonaphthalene (AzNAP), 1-iodonaphthalene (INAP), 1,5-diiodonaphthalene (DIN), and 4,4'-diazidobiphenyl (AzBIPH).

Formalin treatment was performed by diluting concentrated stocks of HIV-1 MN into either phosphate-buffered saline (PBS) or calcium saline buffer, followed by the addition of formalin to achieve the final percentage indicated in the description of FIG. 8. Formalin-treated virus was allowed to sit at 4° C. for more than 4 days before electrophoretic separation using SDS-PAGE as described above.

Infectivity studies with p24 readout: Crosslinking was generally performed as described above. The infectivity assays for the DAN and INA crosslinked viruses with p24 readout, was performed as previously described by Raviv et al., J. Virol. 79(19), 12394-12400 (2005).

Results

As shown in FIG. 7, crosslinking of HIV-1 viral proteins leads to high molecular weight aggregates detectable with anti-gp41 antibodies by western analysis. The lanes in FIG. 7 contain HIV-1 treated as follows: (A) HIV+INA+UV no filter; (B) HIV+INA+UV with filter; (C) HIV+DAN+UV no filter; (D) HIV+DAN+UV with filter; (E) HIV+AzNAP+UV no filter; (F) HIV+INAP+UV no filter; (G) HIV+DIN+UV no filter; (H) HIV+DMSO+UV no filter; (I) HIV control (no DMSO, no UV).

The transmembrane protein (gp41) in HIV-1 exhibited crosslinking and/or aggregation after treatment with hydrophobic crosslinkers INA, DAN, and AzNAP followed by UV irradiation for 15 minutes, as evidenced by a higher molecular weight smear on Western blot (FIG. 7). Little or no high molecular weight aggregation was observed when using hydrophobic molecules that do not crosslink or label proteins, even after UV irradiation for 15 minutes (FIG. 7). Irradiation with ultraviolet light for 2 minutes also gave rise to little or no crosslinking (FIG. 7). When a filter which blocked light of wavelength 360 nm was employed, reduced crosslinking of viral proteins was also observed (FIG. 7).

FIG. 8 shows that the transmembrane protein (gp41) in HIV-1 shows greater crosslinking/aggregation after treatment with hydrophobic crosslinkers and UV irradiation for 15 minutes, than observed when formalin is used. The lanes in FIG. 8 show electrophoretically separated HIV-1 proteins from HIV-1 subjected to the following: (A) HIV+Formalin, 0.02% in PBS; (B) HIV+Formalin, 0.04% in PBS; (C) HIV+Formalin, 0.1% in PBS; (D) HIV+Formalin, 0.03% in Calcium Saline Buffer; (E) HIV+AzBIPH+UV 2 minutes; (F) HIV+INA+UV 2 minutes; (G) HIV+AzBIPH+UV 15 minutes; (H) HIV+INA+UV 15 minutes; (I) HIV+AzBIPH+UV 15 minutes; (J) HIV+INA+UV 15 minutes; (K) HIV+DAN+UV 15 minutes; (L) HIV+AzNAP+UV 15 minutes; (M) HIV+DMSO+UV 15 minutes; (N) HIV control (no DMSO, no UV). Formalin treatments were done using concentrations comparable to those used in the preparation of formalin-inactivated virus vaccines. Accordingly, these results indicate that the hydrophobic crosslinking procedures of the invention are more effective than currently employed formalin treatments for inactivating viruses.

Table 1 shows the results of an infectivity study where the infectivity of DAN crosslinked HIV-1 virions was examined using a sensitive 28-day p24 assay described by Raviv et al., J. Virol. 79(19): 12394-400 (2005) indicates that HIV treated with DAN+UV 15 minutes eliminates residual infectivity.

TABLE 1

Infectivity of HIV Crosslinked with DAN or INA

| HIV-1 Treatment | 28 Day Infectivity Results (SP1426) |
| --- | --- |
| Control | Positive |
| DMSO + UV 2 minutes | Positive |
| DMSO + UV 15 minutes | Positive |
| DAN + UV 2 minutes | Positive |
| DAN + UV 15 minutes | Negative |

TABLE 1-continued

Infectivity of HIV Crosslinked with DAN or INA

| HIV-1 Treatment | 28 Day Infectivity Results (SP1426) |
|---|---|
| INA + UV HIV-1 | Negative |
| Positive Control | Positive |

As illustrated in Table 1, the crosslinking methods of the invention effectively eliminate HIV-1 infectivity as observed by a highly sensitive 28-day infectivity assay.

Example 5

Crosslinking Gives Rise to Detergent Resistance

This Example further demonstrates that the crosslinking methods of the invention give rise to detergent-resistant viral preparations.

Methods

HIV-1 MN was treated using 100 μM of either 1,5-diazidonaphthalene (DAN), 1-azidonaphthalene (AzNAP) or 1-azido-5-iodonaphthalene (INA), plus UV irradiation for 15 minutes, followed by treatment with 1% Triton X-100 at room temperature for 1 hour. The HIV controls were uncrosslinked virus subjected to the same detergent treatment and HIV treated with DMSO and UV irradiation followed by detergent treatment. All detergent-treated viral preparations were passed through a 23% sucrose cushion at 45,000 rpm for 35 minutes (Optima TLX Ultracentrifuge with a TLA 120.1 rotor) to separate crosslinked viral particles from viral proteins present in the supernatant. SDS-PAGE and Western blot analysis were performed on both the supernatant and the pellet fractions of the viral preparation.

Anti-p24 (183-H12-5C, obtained from the National Institutes of Health AIDS Research and Reference Reagent Program (ARRRP) from Dr. Bruce Chesebro and Kathy Wehrly) and anti-gp41 (Chessie 8) were used as primary antibodies for Western analysis. The amount of each protein in the pellet was quantified using AlexaFluor secondary antibodies, and quantitative Western blot analysis using the Odyssey IR imaging software. The terminology "Main spot" in FIG. 9 indicates that integrations were done only for the main protein band (either gp41 or p24) for the samples tested, while the terminology "entire lane" in FIG. 9 indicates that integration was performed for the entire lane for each sample, to include the crosslinked smear. Percent in pellet is expressed as: % in pellet=(pellet integration)/(pellet integration+supernatant integration). p24 samples are the result of one experiment and the gp41 data is combined data from two completely separate experiments (error bars=standard deviation between the two experiments).

Results

FIGS. 9 and 10 illustrate that the amount of sedimented gp41 transmembrane protein and p24 capsid protein, increases when HIV is crosslinked prior to treatment with detergent (1% Triton X-100 at room temperature for 1 hour). The detergent treatment insures that viruses are inactivated by removing viral membrane lipids.

Example 6

Crosslinking of Influenza Viral Proteins

This Example illustrates that the crosslinking methods of the invention are effective for enveloped viruses other than HIV-1, for example, the influenza virus.

Methods

Crosslinking was performed using concentrated influenza stocks (X31/A/AICHI/68, an H3N2 virus, total protein=2 mg/mL) that were obtained from Charles River Laboratories. The concentrated influenza solutions were diluted to 0.5 mg/mL in PBS immediately prior to treatment. The various crosslinkers were prepared using 8 mM stock solutions in DMSO. Each stock was added to 0.5 mg Influenza total protein per ml, to yield a final concentration of 100 micromolar crosslinker. The viral suspension was then UV irradiated for 15 minutes, and the viral proteins were electrophoretically separated by SDS-PAGE under reducing conditions. Western blot was performed using either an anti-HA1 MAb or anti-HA2 (H5N1) polyclonal antibody (eEnzyme), with Coumassie staining to detect all proteins.

Results

Figures 11A, 11B, 11C:
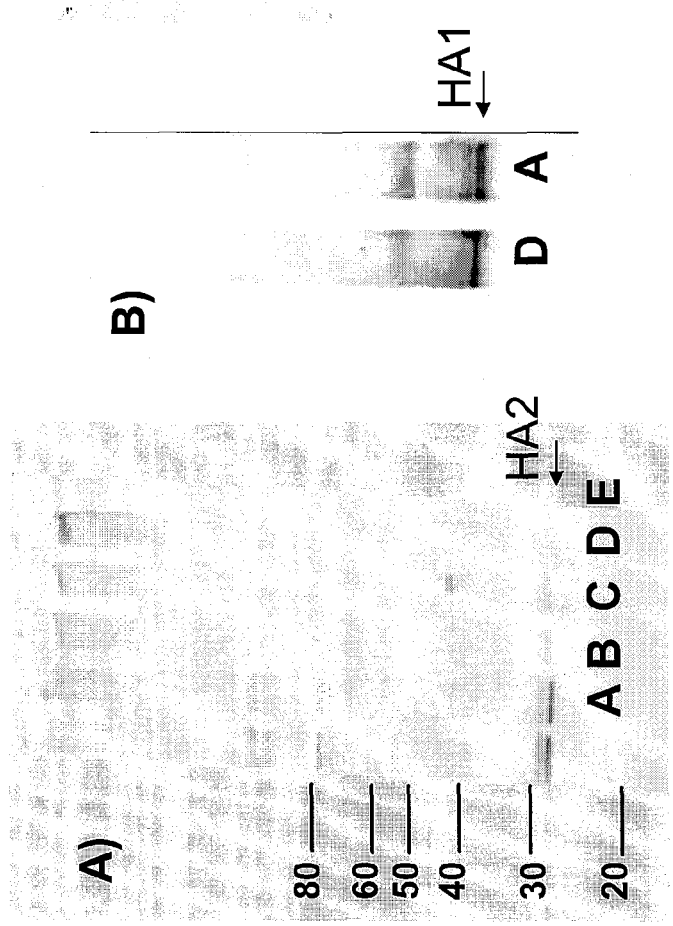
FIG. 11A-C shows that the crosslinking methods of the invention are effective for other enveloped viruses (in addition to HIV-1). Influenza, when treated with 100 micromolar crosslinker+UV irradiation, exhibits crosslinking/aggregation of the transmembrane segment of the (FIG. 11A) HA protein (HA2) whereas (FIG. 11B) the surface segment of HA (HA1) remains untouched. Crosslinking is evidenced by a higher molecular weight smear. Coumassie staining (FIG. 11C) of all the proteins in the virus also supports extensive crosslinking/aggregation in those preparations treated with the crosslinker+UV irradiation. The lanes shown in FIG. 11 represent electrophoretically separated influenza proteins from influenza subjected to the following: (A) Control (No DMSO, No UV); (B) influenza+DMSO+UV 15 minutes; (C) influenza+AzNAP+UV 15 minutes; (D) influenza+DAN+UV 15 minutes; (E) influenza+INA+UV 15 minutes.

FIG. 11A-C illustrates that the crosslinking methods of the invention are also effective in other enveloped viruses such as influenza virus. Influenza, when treated with crosslinker+UV irradiation, exhibits crosslinking/aggregation of the transmembrane segment of the HA protein (HA2) (FIG. 11A). However, FIG. 11B shows that the surface segment of HA (HA1) remains untouched. Crosslinking is evidenced by a higher molecular weight smear. FIG. 11C shows the coumassie stained gel where all the proteins in the virus are evident. These data indicate that extensive crosslinking/aggregation occurs in influenza preparations treated with crosslinkers and UV irradiation pursuant to the methods of the invention.

This Example provides many of the reagents and procedures employed for several experiments described herein.

Example 7

Materials

Antibodies and their sources were as follows: anti-HLA-DR IgG L243 (mAb from Elena Chertova), anti-HLA-DR IgG DA6-147 (mAb from Paul Roche), and anti-Gp32 IgG (rabbit polyclonal Ab from Raoul Benveniste). [$^{125}$I]INA (300 mCi/mmol) was purchased from Lofstrand Laboratories (Gaithersburg, Md.). All other biochemical reagents used were of the highest purity available and were obtained from regular commercial sources.

Viruses

HIV-1$_{MN}$/H9 clone 4 was propagated in H9 cells, as described previously (Ott at al. 1995). SIVmne was obtained from supernatants of the cloned E11 S cell lines derived from a culture of HuT-78 cells infected with SIVmne (Benveniste at al. 1990). Concentrated virus preparations were produced by sucrose gradient banding in a continuous-flow centrifuge (Bess at al. 1997). Inactivation of SIV by treatment with aldrithiol-2 was performed as described (Rossio at al. 1998).

Cell Cultures

Ghost-345 cells (derived from human osteosarcoma cells) that stably express CD4, as well as CXCR4 and CCR5, and NIH3T3 CD4/X4 were obtained from Dan Littman and Vineet KewalRamani. TF228 cells derived from the BJAB human B cell line and that stably express the HIV-1$_{LAI}$ envelope glycoprotein (Jonak at al. 1993) were from Zdenka L. Jonak (Smith-Kline & Beecham, King of Prussia, Pa.). SupT1 (human CD4-expressing T-Lymphoblastic cell line) and TF228 were grown in RPMI supplemented with 10% fetal bovine serum (FBS) (Life Technologies, Inc., Rockville). NIH3T3 CD4 cells were grown in Dulbecco's modified Eagle's medium+10% FBS (D10). NIH3T3 CD4/X4 cells were grown in D10+3 mg/ml puromycin. Ghost 345 cells were grown in D10+500 mg/ml G418+100 mg/ml hygromycin+1 mg/ml puromycin. All the cells were grown in the presence of penicillin and streptomycin.

Treatment with INA

Viruses or cells were suspended in Phosphate Buffered saline (PBS) at a concentration of 0.5-1.0 mg/ml. A stock solution of 30 mM INA in DMSO was prepared. INA was added to the cell or viral suspension under dim light to a final concentration of 1-200 µM. The INA was added so that the total DMSO will not exceed 1% of the total sample volume. Addition of INA was done in installments of 3-4 aliquots while mixing vigorously after each aliquot. The sample was incubated at room temperature for 30 minutes and washed once in PBS.

The suspension was then irradiated with an ozone free 100 W mercury arc lamp and through a water filter to eliminate heat and a 320 nm cut-off filter.

Time of irradiation vary with the size of the sample. For a 1 ml sample and a cross-area of 1 cm$^2$ the irradiation time was 2 minutes. For a 20 ml sample and a cross area of 10 cm$^2$ the irradiation time was 5 minutes.

Labeling of the Target Cells

The fluorescent lipid DiO (Molecular Probes, Eugene, Oreg.) was diluted in 50% Diluent C (Sigma-Aldrich, St. Louis, Mo.) and 50% serum-free RPMI (RPMI) to a final concentration of 50 mM. After two washes in RPMI the cells were incubated in the DiO solution for 30 min at room temperature. They were then washed once with clear RPMI and further incubated 30 min in medium at room temperature. They were then washed three times with PBS, in which they were finally resuspended. At this point [$^{125}$I]INA (1 Ci/mmol) was added in the amount of 10 mCi for each experimental group. Upon 20 min incubation in the dark, the cells were washed with PBS and subsequently used for the photolabeling experiment.

Measurement of Fusion by Photo-sensitized Labeling

The HLA-DR$^+$ virions are incubated with the HLA-DR$^-$ target cells labeled with the fluorescent lipid analog 3,3'-dioctadecyloxacarbocyanine (DiO) and [$^{125}$I]INA for binding at room temperature. Plasma membranes of target cells bearing CD4 and coreceptors are labeled with the fluorescent lipid analog 3 dioctadecyloxacarbocyanine (DiO). [$^{125}$I]INA spontaneously partitions from the medium into viral and other target membranes. In the bound state only integral membrane proteins of the DiO-labeled target membranes react with [$^{125}$I]INA following photoactivation by visible light. Upon incubation of virus-cell complexes at 37° C., DiO becomes part of the viral membrane as a result of fusion and therefore photoactivation using visible light results in covalent attachment of [$^{125}$I]INA to viral membrane-resident proteins. At different times following incubation at 37° C., samples are irradiated with visible light, the cells are lysed, and the HIV or SIV Env, as well other viral envelope-resident proteins such as HLA-DR, is isolated from other radioactively labeled proteins by immunoprecipitation. The extent of radioactivity incorporated into these proteins is then a quantitative measure of viral fusion at the plasma membrane level.

In the case of HIV-1, 1 ml virus (0.79 mg/ml capsid) was added to 3×10$^8$ SupT1 cells in 3 ml. In case of SIVmne, 0.2 ml of virus (0.084 mg/ml capsid) was added to 3 ml medium overlaid on attached Ghost-345 cells. The unbound virions were then removed and the samples subjected to fusion at the desired temperature. At defined times cells were irradiated with an argon laser (Lexel Laser, Inc., Freemont, Calif.) in the multiline mode of 488/514 nm. Suspension cells were irradiated horizontally for two consecutive 10-s periods with a beam of 400 mW that was passed through a UV cut-off filter and focused on an area of 1 cm$^2$ (133 mW/cm$^2$/min). Plated cells were irradiated for 60 s vertically using a 5-W beam focused on an area of 144 cm$^2$ (11 mW/cm$^2$/min).

The cells were then collected and lysed (2% Triton X-100 in Tris-buffered saline (TBS; 50 mM Tris, 138 mM NaCl, 2.7 mM KCl, pH 8) containing protease inhibitors) for 2 h at 4° C. The insoluble material was spun down at 15,000 rpm for 15 min in an Eppendorf microcentrifuge. The supernatant was then diluted twice in TBS and total protein was measured using the BCA protein determination reagent (Pierce, Rockford, Ill.). Samples were subjected to immunoprecipitation using L243 (for HLA-DR) or anti-SW gp32 for the SIV Env. Upon overnight incubation with the respective antibody, protein G-agarose was added for 2 h and washed five times with TBS containing 1% Triton X-100. Proteins were separated by 14% SDS-PAGE and transferred to nitrocellulose membranes. Blots were incubated for 1 h in PBST (phosphate-buffered saline, 0.2% Tween 20) containing 5% powdered skim milk. Membranes were incubated for 2 h with the primary antibody in a 3% BSA solution containing 0.2% Tween 20 and for 1 h 30 min with a peroxidase-conjugated secondary antibody in PBST. Immunoreactivity was detected by using an ECL kit (Amersham, Piscataway, N.J.) and an imaging system with high dynamic range (Bio-Rad GS 505 Molecular Imager System, Hercules, Calif.). The blots were then exposed to Phosphorimager screens; bands were quantified using a Storm system (Molecular Dynamics Sunnyvale, Calif.) and the Image Quant software (Molecular Dynamics).

HIV-1 Envelope Glycoprotein-mediated Cell-cell Fusion

For the photo-sensitized labeling experiments HLA-DR+ TF228.1.16 effector cells and DiO-labeled HLA-DR target cells were loaded with [$^{125}$I]INA and incubated for various times at 37° C. The plates were irradiated for 60 s with a 5-W laser beam over an area of 144 cm$^2$ (11 mW/cm$^2$/min) and incorporation of [$^{125}$I]INA into HLA-DR was measured as described above. For the dye redistribution experiments target cells were labeled with the cytoplasmic dye 5- and 6-([(4-chloromethyebenzoyl]amino) tetramethylrhodamine (CMTMR) at a concentration of 1.5 mM for 1 h at 37° C. Envelope-expressing cells were labeled with calcein AM at a concentration of 1 mM for 1 h at 37° C. Calcein-labeled effector cells were co-cultured with CMTMR-labeled target cells for 2 h at 37° C., and dye redistribution was monitored microscopically as described previously (Munoz-Barroso et al. 1998). The extent of fusion was calculated as:

percent fusion=100×number of bound cells positive for both dyes number of bound cells positive for CMTMR Example 8

INA-Treated SIV Cannot Fuse with Mammalian Cells

This Example describes the results of experiments showing that INA treatment inactivates viruses but leaves them substantially intact. However, such treatment inhibits viral fusion with host cells and prevents viral infection.

FIG. 12 shows a Coomassie-stained SDS-PAGE gel illustrating that treatment of SIV virions with INA causes insubstantial changes in the molecular weights of viral proteins. As shown, exposure to INA at concentrations ranging from 2 µM to 200 µM caused substantially no change in the separation pattern of SIV proteins as compared to untreated virions (DMSO) and virions that were treated with either THE (0.1 M Tris HCl, 0.1 M NaCl, 1 mM EDTA) or 200 µM INA but not exposed to light. Similar results were obtained when these experiments were repeated with HIV. These results indicate that INA treatment maintains the integrity of the majority of viral proteins.

However, as shown by reverse phase HPLC analysis of viral proteins under reducing conditions (FIG. 13), many viral proteins were modified to some extent by INA. As a result, the migration patterns of these viral proteins on the HPLC column were altered. But even though there are some changes in viral proteins after treatment with INA, several major viral proteins were still recognized by monoclonal antibodies directed against those proteins (FIG. 14). Hence, for example, the GP120, P28 and GP32 proteins from INA-treated virions were recognized by monoclonal antibodies directed against the respective untreated proteins.

When 200 µM INA was used to treat SIV, CD4 independent binding of SIV decreased only by 30% (FIG. 15). Binding was measured by incubation of the virus with cells at room temperature. The cells were washed to remove unbound virus and the amount of gp32 that remained attached to the cells was measured by western blot analysis. CD4 dependent binding was not determined. These results show that SW can bind to host cells even though the SW has been treated with INA. These results further illustrate that INA treatment has little effect on the structural integrity and activity of the majority of viral proteins.

However, even though INA-treated virions can bind to host cells, they exhibit reduced fusion with those host cells. As shown by FIG. 16, INA treatment blocked fusion of SIV with the target cell at the plasma membrane level, as measured by a photosensitized labeling method developed by the inventors (see Example 1). Hence, the types of minor structural changes caused by INA treatment appear to be sufficient to undermine the functioning of the viruses.

More significantly, the infectivity of SIV was 100% blocked by treatment with appropriate levels of INA. Table 2 illustrates that INA treatment completely blocks infection of SIV as measured by the expression of the viral protein P-28 at different times after the introduction of the virus. In particular, at 200 µM INA infectivity was blocked by 100%.

TABLE 2

INA Blocks SIV Infectivity

| SAMPLE | SIV P28 (PG/ML) | | |
|---|---|---|---|
| | DAY 3 | DAY 7 | DAY 11 |
| NO Treatment | 5,490 | 156,987 | 179,324 |
| DMSO Treatment | <955 | 71,363 | 94,730 |
| 200 uM INA | <955 | <955 | <955 |
| 20 uM INA | <955 | 1,939 | 32,670 |
| 2 uM INA | <955 | 94,084 | 126,480 |
| 200 uM INA (NO LIGHT) | 4,978 | 124,939 | 200,413 |
| NEG CTRL | <955 | <955 | <955 |

These data indicate that INA treatment gives rise to viral particles that have minor but significant structural changes. The structural changes do not affect the ability of the viral particles to be recognized by antibodies (FIGS. 14 and 18) or bind with host cells (FIG. 15). However, INA treatment does inhibit viral fusion with host cells (FIG. 16). Even more importantly, INA treatment substantially eliminates viral infectivity (Table 2). Hence, INA is a useful reagent for inactivating infectious agents, for example, so that those inactivated infectious agents may be used as vaccines.

Example 9

INA-Treated HIV are Transcriptionally Inactive in Mammalian Cells

This Example describes the results of experiments showing that INA treatment inactivates human immunodeficiency viral transcription, thereby illustrating by another procedure that INA treatment inactivates HIV.

Infectivity assay was carried out using the luciferase reporter gene assay, essentially as described in Spenlehauer, C., Gordon, C., Trkola, A. and Moore, J. (2001) Virology 280, 292-300; and Wei, X., Decker, J., Liu, Z., Zhang, Z., Arani, R., Kilby, M., Saag, M., Wu, X., Shaw, G., and Kappes, J. (2002) Antimicrobial Agents and Chemotherapy, 46, 1896-1905.

Briefly, JC53BL cells were used that express the luciferase enzyme under the transcriptional control of HIV long terminal repeat (LTR). Upon HIV infection the TAT protein from the virus binds to the LTR to induce the expression of Luciferase. The level of Luciferase expression can be assessed by incubation of the sample with a luciferase substrate which triggers a chemiluminescent signal that can be easily quantified by a luminometer.

As shown in FIG. 17, substantially no luciferase expression is detected after JC53BL cells were exposed to INA-treated HIV. However, HIV viruses that were not exposed to INA readily induced expression of luciferase.

These results further demonstrate the effectiveness of INA for inactivating HIV. No effective vaccines are currently available for preventing HIV infection. However, the results provided herein indicate that the present compositions involving INA-inactivated HIV may be useful as vaccines.

Example 10

INA-Treated HIV Bind to Neutralizing Anti-HIV Antibodies

This Example describes the results of experiments showing that INA treatment does not destroy the antigenicity of HIV. Instead, INA-treated HIV readily binds to available anti-HIV neutralizing antibodies.

The antibodies employed were the 2G12 and B12 antibodies that target Gp120 and the 4E10 antibody that targets gp41. Each of these antibody preparations is broadly neutralizing of HIV infectivity.

Antibody binding to HIV virions was measured by an immunocapture procedure essentially as described in Nyambi, P., Burda, S., Bastani, L., and Williams, C. (2001) Journal of Immunological Methods, 253, 253-262. Briefly, 10 microgram of each antibody was coated onto 96 well ELISA plates and non-specific binding was blocked with BSA. HIV was then added and incubated for binding for one hour at 37° C. using different amounts of virus as indicated in FIG. 18. A control assay was performed in which no antibody was used. After washing, the samples were lysed and analyzed for the presence of virus by measuring the viral protein, p24, using an ELISA assay. Each experimental point was carried out in triplicate.

The results are provided in FIG. 18. As shown, FIG. 18 illustrates that INA-treated HIV interacts substantially the same as the non-treated virus with all three antibody preparations. These antibodies were originally derived from human AIDS patients that developed these antibodies spontaneously. Cells producing these antibody preparations were cloned to generate anti-HIV monoclonal antibody preparations. Each of these human monoclonal antibody preparations specifically recognizes structural epitopes on HIV envelope proteins. The 2G12 and B12 antibodies recognize epitopes on the gp120 protein and the 4E10 antibodies recognize an epitope on the gp41 fusion protein. These three antibody clones are broadly neutralizing, i.e. they block infection by many types of HIV in cell culture assays. Hence, these antibodies probe epitopes on HIV that have the potential of inducing antibodies in humans that will block viral infections.

As illustrated herein, each of these antibodies recognizes and binds to INA-inactivated HIV, demonstrating that the epitopes recognized by the antibodies are substantially unaffected by INA treatment.

Example 11

INA-Treated Ebola Viruses Fail to Grow in Mammalian Cells

This Example illustrates that INA inhibits growth of Ebola virus cultured with mammalian cells.

Figure 19:
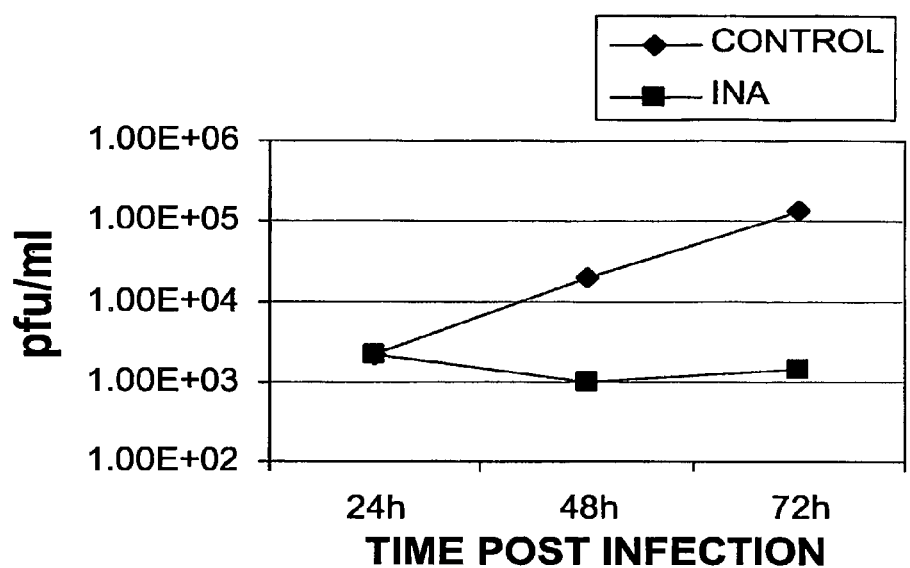
FIG. 19 shows that INA treatment of Ebola viral particles effectively eliminates viral growth in mammalian cells (Vero-E6 cells). Ebola viral particles were incubated with INA or DMSO (Control), exposed to ultraviolet light and then cultured with Vero-E6 cells. At selected time points (shown on the x-axis), aliquots of the virus/cell mixture were removed and the number of viruses (plaque-forming units, pfu) was determined As shown, control-treated Ebola virus grew well on Vero-E6 cells but INA-treated Ebola virus failed to grow.

The EBOV Zaire strain of Ebola virus was used for these studies. Confluent Vero E6 cells were used to monitor the viral replication. $4 \times 10^4$ virus particles (PFUs) were treated with 0.1 mM INA or 0.33% DMSO (control) for 30 min at 4° C. in the dark. After adding 20 mM Glutathione (reduced form, pH 7.5), the viral suspensions were exposed to UV light for 10 minutes. The viral suspensions were then added to cells and incubated for 50 minutes at 37° C. to allow attachment. Subsequently, excess virus was washed and medium added. At the time points indicated in FIG. 19, a fraction of the supernatant was removed and lysed in triazole. Viral RNA was prepared and the particle number was assessed by real time PCR. As shown in FIG. 8, INA-treated viral particles failed to grow in Vero-E6 cells.

These data indicate that INA may be an effective inactivation agent for use in preparing immune system-stimulating compositions of hemorrhagic fever viruses such as Ebola virus.

REFERENCES

Arthur et al. (1998). Chemical inactivation of retroviral infectivity by targeting nucleocapsid protein zinc fingers: A candidate SIV vaccine. AIDS Res. Hum. Retroviruses 14(Suppl. 3), S311-S319.

Arthur et al. (1992). Cellular proteins bound to immunodeficiency viruses: Implications for pathogenesis and vaccines. Science 258, 1935-1938.

Benveniste et al. (1990). Characterization of clones of HIV-1 infected HuT 78 cells defective in gag gene processing and of SIV clones producing large amounts of envelope glycoprotein. J. Med. Prima 19, 351-366.

Bercovici, T, and Gitler, C. (1978). [$^{125}$I]Iodonaphthyl azide, a reagent to determine the penetration of proteins into the lipid bilayer of biological membranes. Biochemistry 17: 1484-89.

Berger, E. A, Murphy, P. M., and Farber, J M. (1999). Chemokine receptors as HIV-1 coreceptors: Roles in viral entry, tropism, and disease. Annu. Rev. Immunol., 657-700.

Bess et al. (1997). Microvesicles are a source of contaminating cellular proteins found in purified HIV-1 preparations. Virology 230, 134-144.

Chan, D. C., Chutkowski, C. T, and Kim, P. S. (1998). Evidence that a prominent cavity in the coiled coil of HIV type 1 gp41 is an attractive drug target. Proc. Natl. Acad. Sci. USA 95: 15613-17.

Chan, D. C., Fass, D., Berger, J M., and Kim, P. S. (1997). Core structure of gp41 from the HIV envelope glycoprotein. Cell 89: 263-273.

Chan, D. C., and Kim, P. S. (1998). HIV entry and its inhibition. Cell 93: 681-684.

Chen, C. H., Matthews, T. J., McDanal, C. B., Bolognesi, D. P., and Greenberg, M. L. (1995). A molecular clasp in the human immunodeficiency virus (HIV) type 1 TM protein determines the anti-HIV activity of gp41 derivatives: Implication for viral fusion. J. Viral. 69: 3771-3777.

Chen, Z., Gettie, A, Ho, D. D., and Marx, P. A (1998). Primary SIVsm isolates use the CCR5 coreceptor from sooty mangabeys naturally infected in west Africa: A comparison of coreceptor usage of primary SIVsm, HIV-2, and SIVmac. Virology 246, 113-124.

Dimitrov, D. S. (2000). Cell biology of virus entry. Cell 101, 697-702.

Dimitrov, D. S., Willey, R., Martin, M., and Blumenthal, R. (1992). Kinetics of HIV-1 interactions with sCD4 and CD4+ cells: Implications for inhibition of virus infection and initial steps of virus entry into cells. Virology 187, 398-406.

Doms, R. W (2000). Beyond receptor expression: The influence of receptor conformation, density, and affinity in HIV-1 infection. Virology 276, 229-237.

Duzgunes, N., Larsen, C. E., Konopka, K., Alford, D. R., Young, L. J., McGraw, T. P., Davis, B. R., Nir, S., and Jennings, M. (1991). Fusion of HIV-1 and SIVmac with liposomes and modulation of HIV-1 infectivity. Adv. Exp. Med. Biol. 300, 167-189.

Frey, S., Marsh, M., Gunther, S., Pelchen-Matthews, A, Stephens, P., Ortlepp, S., and Stegmann, T (1995). Temperature dependence of cell-cell fusion induced by the envelope glycoprotein of human immunodeficiency virus type 1. J. Virol., 1462-72.

Furuta, R. A., Wild, C. T, Weng, Y, and Weiss, C. D. (1998). Capture of an early fusion-active conformation of HIV-1 gp41. Nat. Struct. Biol. 5: 276-279.

Gallo, S. A., Puri, A, and Blumenthal, R. (2001). HIV-1 gp41 six-helix bundle formation occurs rapidly after the engagement of gp120 by CXCR4 in the HIV-1 Env-mediated fusion process. Biochemistry 40:12231-12236.

Hoekstra, D., de Boer, T, Klappe, K., and Wilschut, J (1984). Fluorescence method for measuring the kinetics of fusion between biological membranes. Biochemistry 23, 5675-5681.

Hug, P., Lin, H. M., Korte, T, Xiao, X., Dimitrov, D. S., Wang, J M., Puri, and Blumenthal, R. (2000). Glycosphingolipids promote entry of a broad range of human immunodeficiency virus type 1 isolates into cell lines expressing CD4, CXCR4, and/or CCR5. J. Virol., 74: 6377-6385.

Jernigan, K. M, Blumenthal, R., and Puri, A (2000). Varying effects of temperature, Ca(2+) and cytochalasin on fusion activity mediated by human immunodeficiency virus type 1 and type 2 glycoproteins. FEBS Lett. 474, 246-251.

Jiang, S., Lin, K., Strick, N., and Neurath, A R. (1993) Inhibition of HIV-1 infection by a fusion domain binding peptide from the HIV-1 envelope glycoprotein GP41. Biochem. Biophys. Res. Commun. 195, 533-538.

Jonak, Z. L., Clark, R. K., Matour, D., Trulli, S., Craig, R., Henri, E., Lee, E. V., Greig, R., and Debouck, C. (1993). A human lymphoid recombinant cell line with functional human immunodeficiency virus type envelope. AIDS Res. Hum. Retroviruses, 9: 23-32.

Kowalski, M., Potz, J, Basiripour, L., Dorfman, T, Goh, W C., Terwilliger, Dayton, A, Rosen, C., Haseltine, W, and Sodroski, J (1987). Functional regions of the envelope glycoprotein of human immunodeficiency virus type 1. Science 237, 1351-1355.

Krumbiegel, M., Herrmann, A, and Blumenthal, R. (1994). Kinetics of the low-pH induced conformational changes and fusogenic activity of influenza hemagglutinin. Biophys. J. 67, 2355-2360.

LaCasse, R. A, Follis, K. E., Trahey, M., Scarborough, J. D., Littman, D. R., and Nunberg, J H. (1999). Fusion-competent vaccines: Broad neutralization of primary isolates of HIV. Science 283, 357-362.

Liao, Z., Roos, J. W., and Hildreth, J. E. (2000). Increased infectivity of HIV type 1 particles bound to cell surface and solid-phase ICAM-1 and VCAM-1 through acquired adhesion molecules LFA-1 and VLA-4. AIDS Res. Hum. Retroviruses 16, 355-366.

Lifson, J D., Feinberg, M. B., Reyes, G. R., Rabins, L., Banapour, B. Chakrabarti, S., Moss, B., Wong-Staal, F., Steimer, K. S., and Engleman, E. G. (1986). Induction of CD4-dependent cell fusion by the HTLV-III/LAV envelope glycoprotein. Nature 323, 725-728.

Melikyan, G. B., Markosyan, R. M., Hemmati, H., Delmedico, M. K., Lambert, D. M., and Cohen, F. S. (2000). Evidence that the transition of HIV-1 gp41 into a six-helix bundle, not the bundle configuration, induces membrane fusion. J. Cell Biol. 151: 413-423.

Merezhinskaya, N., Kuijpers, G. A, and Raviv, Y. (1998). Reversible penetration of alpha-glutathione S-transferase into biological membranes revealed by photosensitized labeling in situ. Biochem. J. 335, 597-604.

Munoz-Barroso, I., Durell, S., Sakaguchi, K., Appella, E., and Blumenthal, R. (1998). Dilation of the human immunodeficiency virus-1 envelope glycoprotein fusion pore revealed by the inhibitory action of a synthetic peptide from gp41. J. Cell Biol. 140, 315-323.

Ott, D. E., Nigida, S. M., Jr., Henderson, L. E, and Arthur, L. O. (1995). The majority of cells are superinfected in a cloned cell line that produces high levels of human immunodeficiency virus type 1 strain MN. J. Virol. 69, 2443-2450.

Pak, C. C., Krumbiegel, M., Blumenthal, R., and Raviv, Y. (1994). Detection of influenza hemagglutinin interaction with biological membranes by photosensitized activation of [$^{125}$I]Iodonaphthylazide. J. Biol. Chem. 269, 14614-14619.

Pak, C. C., Puri, A., and Blumenthal, R. (1997). Conformational changes and fusion activity of vesicular stomatitis virus glycoprotein: [$^{125}$I]Iodonaphthylazide photo labeling studies in biological membranes. Biochemistry 36, 8890-8896.

Raviv, Y., Bercovici, T. and Salomon, Y. (1984) Biochemistry 23: 503-508.

Raviv, Y., Bercovici, T., Gitler, C., and Salomon, Y. (1989). Detection of nearest neighbors to specific fluorescently tagged ligands in rod outer segment and lymphocyte plasma membranes by photosensitization of 5-iodonaphthyl 1-azide. Biochemistry 28, 1313-1319.

Raviv, Y., Pollard, H. B., Bruggemann, E. P., Pastan, I., and Gottesman, M. M. (1990). Photosensitized labeling of a functional multidrug transporter in living drug-resistant tumor cells. J. Biol. Chem. 265, 3975-3980.

Raviv, Y., Puri, A., and Blumenthal, R. (2000). P-glycoprotein-overexpressing multidrug-resistant cells are resistant to infection by enveloped viruses that enter via the plasma membrane. FASEB J. 14: 511-515.

Raviv, Y., Salomon, Y., Gitler, C., and Bercovici, T. (1987). Selective labeling of proteins in biological systems by photosensitization of iodonaphthalene-1-azide. Proc. Natl. Acad. Sci. USA 84, 6103-6107.

Raviv, Y., Viard, M., Bess Jr., J. and Blumenthal, R. (2002) Virology 293: 243-351.

Rossio, J. L., Esser, M. T, Suryanarayana, K., Schneider, D. K., Bess, J. W., Jr., Vasquez, G. M., Wiltrout, T. A, Chertova, E., Grimes, M. K., Sattentau, Q., Arthur, L. O., Henderson, L. E., and Lifson, J D. (1998). Inactivation of human immunodeficiency virus type 1 infectivity with preservation of conformational and functional integrity of virion surface proteins. J. Virol. 72: 7992-8001.

Ugolini, S., Mondor, I., and Sattentau, Q. J. (1999). HIV-1 attachment: Another look. Trends Microbiol. 7: 144-149.

Volsky, D. J. (1990). Fusion of human immunodeficiency virus type 1 (HIV-1) with human cells as measured by membrane fluorescence dequenching (DQ) method: Roles of HIV-cell fusion in AIDS pathogenesis. In "Horizons in Membrane Biotechnology," pp. 179-198, Wiley-Liss, New York.

Weissenhorn, W., Dessen, A., Harrison, S. C., Skehel, J. J, and Wiley, D. C. (1997). Atomic structure of the ectodomain from HIV-1 gp41. Nature 387, 426-428.

Wild, C., Greenwell, T, and Matthews, T (1993). A synthetic peptide from HIV-1 gp41 is a potent inhibitor of virus-mediated cell-cell fusion. AIDS Res. Hum. Retroviruses 9, 1051-1053.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed:

1. A method for inactivating a viral population, wherein the viral population comprises HIV, SIV, Ebola, or influenza, comprising:
   (a) forming a mixture by contacting the viral population with a compound that is:

1,5-diazidonaphthalene DAN 1-azidonaphthalene AzNAP 1-azido-5-iodonaphthalene INA 4,4'-diazidobiphenyl" AzBIPH or a mixture thereof;
   (b) exposing the mixture to irradiation to crosslink viral proteins and generate a photocrosslinked viral preparation; and
   (c) removing lipids from viral membranes before or after steps (a) and (b) by extracting the photocrosslinked viral preparation with a detergent, to thereby inactivate the viral population.

2. The method of claim 1, wherein the mixture is exposed to ultraviolet irradiation.

3. The method of claim 2, wherein the ultraviolet irradiation is for about 2 to about 30 minutes.

4. The method of claim 2, wherein the ultraviolet irradiate is for about 10 to about 20 minutes.

5. The method of claim 1, wherein the mixture is exposed to visible light irradiation in the presence of a photosensitizer chromophore.

6. The method of claim 5, wherein the photosensitizer chromophore has an absorption maxima in the range of about 450 to about 525 nm or about 600 to about 700 nm.

7. The method of claim 5, wherein the photosensitizer chromophore is a porphyrin, chlorin, bacteriochlorin, purpurin, phthalocyanine, naphthalocyanine, merocyanines, carbocyanine, texaphyrin or non-tetrapyrrole.

8. The method of claim 1, wherein the detergent is polyoxyethylene covalently linked to a fatty acid, polysorbate 80, polysorbate 20, oxyethylated alkylphenol or sodium dodecyl sulfate when step (c) is performed after steps (a) and (b).

9. The method of claim 1, wherein the detergent comprises a compound of the formula:

wherein n is an integer of 9 or 10.

10. The method of claim 1, wherein the detergent is beta-cyclodextrin and methyl-beta-cyclodextrin, when step (c) is performed before steps (a) and (b).

11. The method of claim 1, wherein the detergent is an aqueous solution of about 0.001% to about 10% detergent.

12. The method of claim 1, wherein the detergent also removes uncrosslinked proteins.

13. A composition comprising a viral preparation prepared by the method of claim 1.

14. A method for inactivating a population of HIV, SIV, Ebola, or influenza viruses comprising:
   (a) contacting the population with a compound of any of the following structures, or a mixture thereof:

1,5-diazidonaphthalene    1-azido-5-iodonaphthalene

-continued

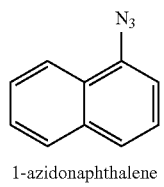
1-azidonaphthalene

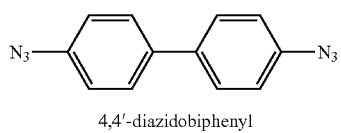
4,4'-diazidobiphenyl to generate a mixture of the compound(s) and the viral particles;
(b) exposing the mixture to ultraviolet irradiation to crosslink viral membrane proteins to generate a photocrosslinked viral preparation; and
(c) removing lipids from viral membranes by extracting the photocrosslinked viral preparation with an aqueous solution of an oxyethylated alkylphenol detergent;
to thereby inactivate a population of enveloped viruses.

15. The method of claim 14, wherein the detergent has the structure:

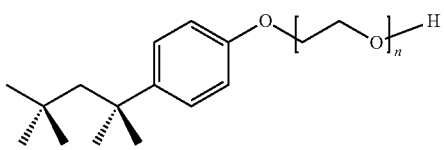

wherein n is an integer of 9 or 10.

16. The method of any of claim 14, wherein the detergent is an aqueous solution of about 0.1% to about 3% detergent.

17. A composition comprising a viral preparation prepared by the method of claim 14.

* * * * *